(12) United States Patent
Wang et al.

(10) Patent No.: US 7,767,817 B2
(45) Date of Patent: Aug. 3, 2010

(54) WATER SOLUBLE BORONIC ACID FLUORESCENT REPORTER COMPOUNDS AND METHODS OF USE THEREOF

(76) Inventors: Binghe Wang, 1222 Rosette Way, Marietta, GA (US) 30062; Xingming Gao, 1234-310 Defoor Village Ct., Atlanta, GA (US) 30318; Wenqian Yang, 308 Sylvan Way, Chapel Hill, NC (US) 27516; Hao Fang, 2319D Briarcliff Rd., NE., Atlanta, GA (US) 30329; Jun Yan, 193-B Tusculum Dr., Oak Ridge, TN (US) 37830

( * ) Notice: Subject to any disclaimer, the term of this patent is extended or adjusted under 35 U.S.C. 154(b) by 618 days.

(21) Appl. No.: 10/570,807

(22) PCT Filed: Sep. 7, 2004

(86) PCT No.: PCT/US2004/028838
§ 371 (c)(1),
(2), (4) Date: May 31, 2007

(87) PCT Pub. No.: WO2005/024416
PCT Pub. Date: Mar. 17, 2005

(65) Prior Publication Data
US 2007/0274922 A1    Nov. 29, 2007

Related U.S. Application Data

(60) Provisional application No. 60/500,785, filed on Sep. 5, 2003.

(51) Int. Cl.
C07D 215/00 (2006.01)
C07D 215/12 (2006.01)
(52) U.S. Cl. ........................ 546/152; 546/176
(58) Field of Classification Search .............. 546/152, 546/176
See application file for complete search history.

(56) References Cited

U.S. PATENT DOCUMENTS

| 5,266,493 | A | 11/1993 | Young |
| 7,201,892 | B2 * | 4/2007 | Achilefu et al. ............... 424/9.6 |
| 2004/0044258 | A1 | 3/2004 | Shoda et al. |

OTHER PUBLICATIONS

Goldman et al. Analytical Chemistry (1970), 42(11), 1186-8.*
Adhikiri et al. Tetrahedron Letters, (1999), 40, 7893-7896.*
Yang et al. Bioorganic & Medicinal Chemistry Letters (2003), 13(6), 1019-1022.*
Devi P. Adhikiri and Michael D. Heagy; "Fluorescent chemosensor for carbohydrates which shows large change in chelation-enhanced quenching"; Tetrahedron Letters 40 (1999) 7893-7896.

* cited by examiner

*Primary Examiner*—Janet L Andres
*Assistant Examiner*—Nizal S Chandrakumar
(74) *Attorney, Agent, or Firm*—Gardner Groff Greenwald & Villanueva, PC

(57) ABSTRACT

Described herein are boronic acid fluorescent compounds and methods of use thereof.

2 Claims, 19 Drawing Sheets

(A)

(B)

WATER SOLUBLE BORONIC ACID FLUORESCENT REPORTER COMPOUNDS AND METHODS OF USE THEREOF

CROSS REFERENCE TO RELATED APPLICATIONS

This application claims the benefit of U.S. provisional application Ser. No. 60/500,785 filed Sep. 5, 2003. This application is hereby incorporated by this reference in its entirety for all of its teachings.

ACKNOWLEDGEMENTS

The research leading to this invention was funded in part by the National Institutes of Health, Grant Nos. CA88343, NO1-CO-27184, and DK55062. The U.S. Government may have certain rights in this invention.

BACKGROUND

Saccharides play important roles in biological processes. During the last decade, much effort has been directed toward developing fluorescent chemosensors for detecting saccharides. One issue to the design of such sensors is the availability of fluorescent reporter moieties that respond to the saccharide recognition event with significant fluorescence intensity changes. Another issue in the synthesis of such sensors is the low water solubility of most fluorescent reporter compounds that are used for making fluorescent sensors.

The use of fluorescent sensors for cell-surface polysaccharides for in vivo, in vitro, and other biological applications is particularly attractive. The additional requirements for a sensor functional in vivo, in vitro, and other biological applications include: (1) reasonable water solubility; (2) optimal fluorescence intensity changes at physiological pH; and (3) chemical and photochemical stability.

Boronic acids have been known for decades to bind saccharides via covalent interaction. The most common interactions are with cis-1,2- or 1,3-diols of saccharides to form five- or six-membered rings, respectively. During the last decade, progress has been made in the construction of boronic acid-based sensors for carbohydrates. Different mechanisms have been used to induce spectroscopic changes upon binding of the boronic acid moiety with a saccharide. Among the most important discoveries is an anthracene-based fluorescent reporter system developed by Shinkai and co-workers. See T. D. James, K. R. A. S. Sandanayake, and S. Shinkai, *Chem. Commun.* 1994, 477-78; K. R. A. S. Sandanayake and S. Shinkai, *J. Chem. Soc. Chem. Commun.* 1994, 1083-84. This anthracene-based system has been widely used because of its fairly large fluorescence intensity increase upon ester formation due to the switching of a photoinduced electron transfer (PET) process.

The anthracene-based fluorescent reporter, however, has many undesirable properties, such as low water solubility and poor photochemical stability. For such sensors to be useful in a biological system and/or testing, it is essential that they function under near physiological conditions. One such fluorescent saccharide sensor, 8-quinolineboronic acid (8-QBA), responds to the binding of a carbohydrate with unprecedented large increases in fluorescence intensity at physiological pH in aqueous solution. See W. Yang, J. Yan, G. Springsteen, and B. Wang, *Bioorg. Med. Chem. Lett.* 2003, 13, 1019-1022.

Described herein are water soluble, boronic acid fluorescent reporter compounds that can be used as sensors for a variety of small molecule analytes and macromolecules such as, for example, carbohydrates and glycosylated macromolecules including glycolipids, glycoproteins. The compounds described herein are sufficiently water soluble and exhibit very large fluorescence intensity changes upon binding to a macromolcule. The use of these compounds as potential fluorescent sensors for small molecule analytes and macromolecules, such as saccharides, takes advantage of the hybridization state change of the boron upon binding to these molecules at physiological pH, which causes a change in the spectroscopic properties of the boron-containing compounds.

SUMMARY

Described herein are boronic acid fluorescent reporter compounds and methods of use thereof. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below. Like numbers represent the same elements throughout the figures.

DETAILED DESCRIPTION

Figure 1:
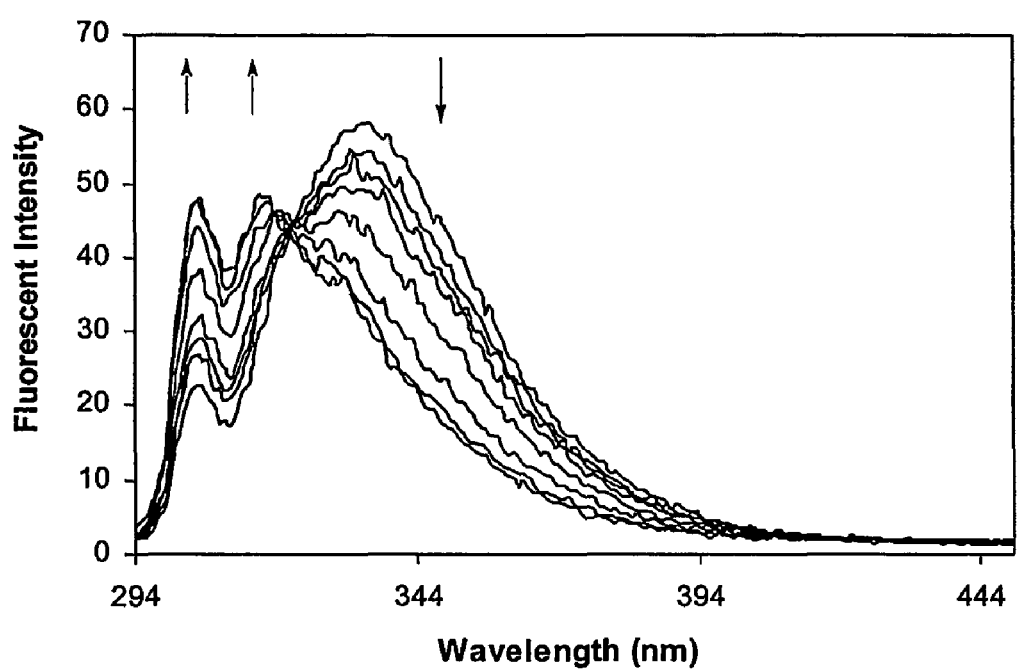
FIG. 1 shows the fluorescence spectra of 5 ($1 \times 10^{-5}$ M; Table 1) upon addition of D-fructose (0, 0.1, 0.2, 0.4, 1.0, 2.0, 4.0, 5.0 mM) in 0.1 M phosphate buffer at pH 7.4: $\lambda_{ex}$=274 nm.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

The term "independently" when referring to two or more particular R groups present in a formula refers to any combination of variables listed for that particular R group. For example, in the formula —NRR', where R and R' are, independently, hydrogen, methyl, or ethyl, any combination of R and R' is contemplated. Thus, for example, when R is hydrogen, R' can be hydrogen, methyl, or ethyl.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Variables such as $R^1$-$R^9$, X, Y, and Z used throughout the application are the same variables as previously defined unless stated to the contrary.

By "subject" is meant an individual. The subject can be a mammal such as a primate or a human. The term "subject" can include domesticated animals including, but not limited to, cats, dogs, etc., livestock (e.g., cattle, horses, pigs, sheep, goats, etc.), and laboratory animals (e.g., mouse, rabbit, rat, guinea pig, etc.).

By "contacting" is meant an instance of exposure by close physical contact of at least one substance to another substance.

The term "alkyl group" as used herein is a branched or straight chain saturated hydrocarbon group of 1 to 15 carbon atoms, such as methyl, ethyl, n-propyl, isopropyl, n-butyl, isobutyl, t-butyl, pentyl, hexyl, heptyl, octyl, decyl, or tetradecyl, and the like. A "lower alkyl" group is an alkyl group containing from one to six carbon atoms.

The term "alkoxy" as used herein is an alkyl group bound through a single, terminal ether linkage; that is, an "alkoxy" group may be defined as —OR where R is alkyl as defined above. A "lower alkoxy" group is an alkoxy group containing from one to six carbon atoms.

The term "alkenyl group" as used herein is a hydrocarbon group of from 2 to 24 carbon atoms and structural formula containing at least one carbon-carbon double bond. Asymmetric structures such as (AB)C═C(CD) are intended to include both the E and Z isomers. This may be presumed in structural formulae herein wherein an asymmetric alkene is present, or it may be explicitly indicated by the bond symbol C.

The term "alkynyl group" as used herein is a hydrocarbon group of 2 to 24 carbon atoms and a structural formula containing at least one carbon-carbon triple bond.

The term "amino group" as used herein is defined as —NH$_2$. The term "alkyl substituted amino group" is defined herein as amino group having one or two alkyl groups as defined above. For example, the alkyl substituted amino group can be mono- or disubstituted with a lower alkyl group, where when the amino group is disubstituted, the alkyl groups can be the same or different.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aralkyl" as used herein is an aryl group having an alkyl, alkynyl, or alkenyl group as defined above attached to the aromatic group. An example of an aralkyl group is a benzyl group.

The term "hydroxyalkyl group" as used herein is an alkyl, alkenyl, alkynyl, aryl, aralkyl, cycloalkyl, halogenated alkyl, or heterocycloalkyl group described above that has at least one hydrogen atom substituted with a hydroxyl group.

The term "alkoxyalkyl group" is defined as an alkyl, alkenyl, alkynyl, aryl, aralkyl, cycloalkyl, halogenated alkyl, or heterocycloalkyl group described above that has at least one hydrogen atom substituted with an alkoxy group described above.

The term "aminoalkyl group" as used herein is an alkyl, alkenyl, alkynyl, aryl, aralkyl, cycloalkyl, or heterocycloalkyl group described above that has at least one hydrogen atom substituted with an amino group or an alkyl substituted amino group.

The term "ester" as used herein is represented by the formula —C(O)OA, where A can be an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH.

The term "ester" as used herein is represented by the formula —OC(O)R, where R can be an alkyl, alkenyl, alkynyl, aryl, aralkyl, cycloalkyl, halogenated alkyl, or heterocycloalkyl group described above.

The term "aldehyde" as used herein is represented by the formula —C(O)H.

The term "keto group" as used herein is represented by the formula —C(O)R, where R is an alkyl, alkenyl, alkynyl, aryl, aralkyl, cycloalkyl, or heterocycloalkyl group described above.

The term "nitrile group" as used herein is represented by the formula —CN.

The term "nitro group" as used herein is represented by the formula —NO$_2$.

The term "halogen" as used herein includes fluorine, chlorine, bromine, or iodine.

The term "thiol ether group" as used herein as —SR where R is an alkyl, alkenyl, alkynyl, aryl, aralkyl, cycloalkyl, or heterocycloalkyl group described above.

The term "amide" as used herein is represented by the formula —C(O)NRR', where R and R' can be, independently, hydrogen, an alkyl, alkenyl, alkynyl, aryl, aralkyl, cycloalkyl as described above.

The term "sulfo-oxo group" as used herein is represented by the formulas —S(O)$_2$R, —OS(O)$_2$R, or, —OS(O)$_2$OR, where R can be hydrogen, an alkyl, alkenyl, alkynyl, aryl, aralkyl, cycloalkyl, halogenated alkyl, or heterocycloalkyl group described above.

The term "sulfo-amide group" as used herein is represented by the formulas —S(O)$_2$NR or —OS(O)$_2$NR, where R can be hydrogen, an alkyl, alkenyl, alkynyl, aryl, aralkyl, cycloalkyl, halogenated alkyl, or heterocycloalkyl group described above.

The term "phosphate" is represented by the formula (RO)$_2$(O)PO—, where each R can be, independently, hydrogen, an alkyl, alkenyl, alkynyl, aryl, aralkyl, cycloalkyl, halogenated alkyl, heterocycloalkyl group as described above, or the salt thereof.

The term "phosphonate" is represented by the formula (RO)(R)PO—, where each R and R can be, independently, hydrogen, an alkyl, alkenyl, alkynyl, aryl, aralkyl, cycloalkyl, halogenated alkyl, heterocycloalkyl group as described above, or the salt thereof.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Additionally, if a generic formula has several variables, each and every combination of the variables in the formula is contemplated. For example, if an aryl ring is substituted with one or more $C_1$-$C_{15}$ alkyl groups, then every possible substitution about the aryl ring with respect to the different alkyl groups is contemplated.

I. Compositions a. Boronic Acid Fluorescent Compounds

Described herein are boronic acid fluorescent compounds. In one aspect, the compounds have the formula II

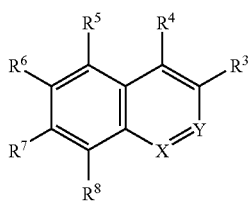

wherein X is O, S, CR$^1$, NR$^2$, or N;
wherein when Y is present, Y is CR$^9$ or N and X is CR$^1$ or N;
wherein when Y is not present, X is O, S, C(R$^1$)$_2$, or NR$^2$;
wherein R$^1$-R$^9$ are, independently, hydrogen, a branched or straight chain alkyl group, a hydroxyl group, an alkoxy group, a COOH group, a B(OH)$_2$ group, an alkyl substituted amino group, an amino group, a hydroxyalkyl group, an alkoxyalkyl group, an aminoalkyl group, a thiol group, a thiol ether group, an amide group, an aldehyde group, a ketone group, an ester, an arakyl group, an aryl group, a nitrile group, a nitro, a halogen, a sulfo-oxo group, a sulfoamide group, a phosphonate group, or a phosphate;
wherein the compound having the formula II has at least one B(OH)$_2$ group directly or indirectly bonded to the ring;

or the salt thereof.

The compounds having the formula II have at least one B(OH)$_2$ group directly or indirectly bonded to one of the fused rings in formula II. When the B(OH)$_2$ group is attached to one of the carbon atoms of the ring, it is "directly" attached to the ring. Conversely, when the B(OH)$_2$ group is attached to a carbon atom of the ring of formula II through another atom or group, the B(OH)$_2$ group is "indirectly attached to the ring. For example, the B(OH)$_2$ group can be attached to an aryl group, and the aryl group is attached to one of the ring carbons in formula II.

In one aspect, Y in formula II is CR$^9$. In another aspect, Y in formula II is CR$^9$ and X is CR$^1$. In another aspect, Y in formula II is CR$^9$, and X is CR$^1$, where R$^1$ is B(OH)$_2$. In a further aspect, Y in formula II is CR$^9$, X is CR$^1$, where R$^1$ is B(OH)$_2$, wherein at least one of R$^3$-R$^9$ is an alkyl substituted amino group. In a further aspect, Y in formula II is CR$^9$, X is CR$^1$, where R$^1$ is B(OH)$_2$, and R$^4$ is an alkyl substituted amino group such as, for example, NMe$_2$. In a further aspect, Y in formula II is CR$^9$, X is CR$^1$, where R$^1$ is B(OH)$_2$, R$^4$ is NMe$_2$, and R$^3$ and R$^5$-R$^9$ are hydrogen.

In another aspect, Y in formula II is CR$^9$, X is CR$^1$, where R$^1$ is B(OH)$_2$, and R$^5$ is an alkyl substituted amino group such as, for example, NMe$_2$. In a further aspect, Y in formula II is CR$^9$, X is CR$^1$, where R$^1$ is B(OH)$_2$, R$^5$ is NMe$_2$, and R$^3$, R$^4$, and R$^6$-R$^9$ are hydrogen.

In another aspect, Y in formula II is CR$^9$, X is CR$^1$, where R$^9$ is B(OH)$_2$, and R$^6$ is an alkyl substituted amino group such as, for example, NMe$_2$. In a further aspect, Y in formula II is CR$^9$, X is CR$^1$, where R$^9$ is B(OH)$_2$, R$^6$ is NMe$_2$, and R$^3$-R$^5$ and R$^7$-R$^9$ are hydrogen.

In one aspect, X in formula II is N and Y is CR$^9$. In another aspect, X in formula II is N, Y is CR$^9$, and R$^3$ is B(OH)$_2$. In a further aspect, X in formula II is N, Y is CR$^9$, R$^3$ is B(OH)$_2$, and R$^4$-R$^9$ are hydrogen.

In another aspect, X in formula II is CR$^1$, Y is N, and R$^4$ is B(OH)$_2$. In a further aspect, Y in formula II is N, Y is CR$^1$, R$^4$ is B(OH)$_2$, and R$^3$ and R$^5$-R$^9$ are hydrogen.

In another aspect, X in formula II is N, Y is CR$^9$, and R$^5$ is B(OH)$_2$. In a further aspect, X in formula II is N, Y is CR$^9$, R$^5$ is B(OH)$_2$, and R$^3$, R$^4$, and R$^6$-R$^9$ are hydrogen.

In another aspect, X in formula II is N, Y is CR$^9$, and R$^6$ is B(OH)$_2$. In a further aspect, X in formula II is N, Y is CR$^9$, R$^6$ is B(OH)$_2$, and R$^3$-R$^5$ and R$^7$-R$^9$ are hydrogen.

In a further aspect, X in formula II is N, Y is CR$^9$, and R$^7$ is B(OH)$_2$. In another aspect, X in formula II is N, Y is CR$^9$, R$^7$ is B(OH)$_2$, and R$^3$-R$^6$, R$^8$, and R$^9$ are hydrogen.

In another aspect, X in formula II is N, Y is CR$^9$, and R$^8$ is B(OH)$_2$. In a further aspect, X in formula II is N, Y is CR$^9$, R$^8$ is B(OH)$_2$, and R$^3$-R$^7$ and R$^9$ are hydrogen.

In one aspect, when X in formula II is N and Y is CR$^9$, at least one R$^3$-R$^9$ group is COOH. In another aspect, when X in formula II is N, Y is CR$^9$, and at least one R$^3$-R$^9$ group is COOH, then at least one R$^3$-R$^9$ group is Z-B(OH)$_2$, where Z is an aryl group. In this aspect, Z can be, for example, a substituted or unsubstituted phenyl ring. In another aspect, X in formula II is N, Y is CR$^9$, R$^4$ is COOH, and R$^1$ is p-phenyl-B(OH)$_2$. In a further aspect, X in formula II is N, Y is CR$^9$, R$^4$ is COOH, R$^1$ is p-phenyl-B(OH)$_2$, and R$^3$ and R$^5$-R$^9$ are hydrogen.

In another aspect, Y in formula II is not present and X is sulfur. In one aspect, Y in formula II is not present, X is sulfur, and R$^3$ is B(OH)$_2$. In a further aspect, Y in formula II is not present, X is sulfur, R$^3$ is B(OH)$_2$, and R$^4$-R$^8$ are hydrogen.

In one aspect, the compounds having the formula II are depicted in Table 1.

TABLE 1

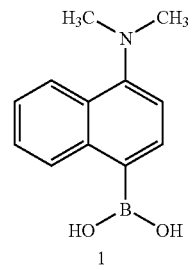

1

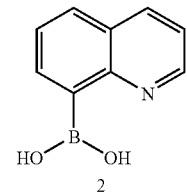

2

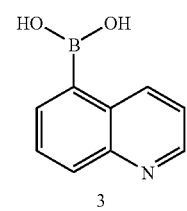

3

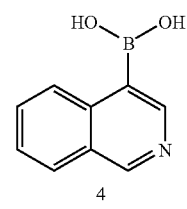

4

TABLE 1-continued

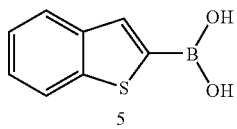

5

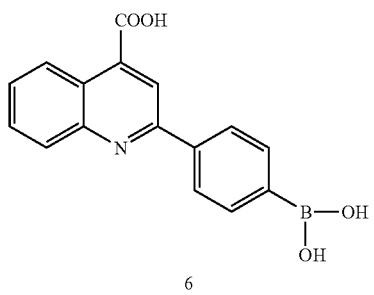

6

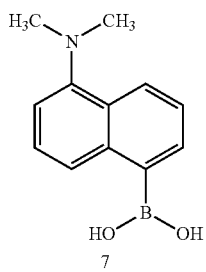

7

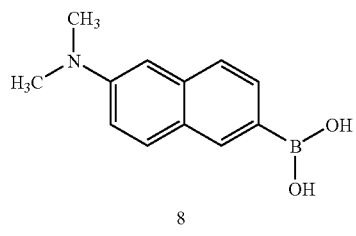

8

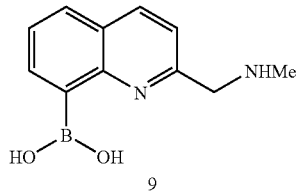

9

In another aspect, the compound having the formula II is not 1-naphthalenyl boronic acid; 2-naphthalenyl boronic acid; 6-dimethylamino-2-naphthalenyl boronic acid boronic acid; 6-amino-2-naphthalenyl boronic acid boronic acid; 8-quinolineboronic acid; benzo[b]thiophene-2-boronic acid; 2-(4-phenylboronic acid)-quinoline-4-carboxylic acid; N-Boc-4-amino-1-naphthalene boronic acid; 4-cyano-1-naphthalenyl boronic acid; 6-((diphenylamino)-2-naphthalenyl)boronic acid; 5-bis-(phenylmethoxy)(ethyl)amino-2-naphthalenyl-boronic acid; 6-bis-(phenylmethoxy)(ethyl)amino-2-naphthalenyl-boronic acid; 6-((naphthalenylphenylamino)-2-naphthalenyl)boronic acid; 6-((1,1'-biphenyl-4-ylphenylamino)-2-naphthalenyl)boronic acid; 6-(2-naphthalenylphenylamino)-2-naphthalenyl)boronic acid; phenylmether ester of 4-borono-1-naphthalenyl carbamic acid; 6-cyano-1-naphthalenyl boronic acid; 4-(2,2-dimethyl-1-oxopropyl)amino-1-naphthalenyl boronic acid; 1-(diethylamino carbonyl)-2-naphthalenyl boronic acid; 4-(cyclopropyhnethyl)propylamino-1-naphthalenyl boronic acid; 1-bis-(1-methylethyl)amino carbonyl)-2-naphthalenyl boronic acid; and 3-bis-(1-methylethyl)amino carbonyl)-4-methoxy-2-naphthalenyl boronic acid.

One advantage of the boronic acid compounds described herein is that they possess good solubility in water. Prior art boronic acid complexes have low solubility, which makes their use in physiological conditions difficult to impractical. In one aspect, the compounds described herein have a solubility of greater than 1 μM, greater than 5 μM, or greater than 10 μM in water. In another aspect, the compounds described herein have a solubility of from 1 μM to 1.2 mM, 1 μM to 1 mM, 1 μM to 0.8 mM, 1 μM to 0.6 mM, 1 μM to 0.4 mM, or 1 μM to 0.2 mM.

The compounds having the formula II can be prepared using techniques known in the art. For example, naphthalene, quinoline (X=N and Y=CH), or isoquinoline (X=CH and Y=N) that has a halide bonded to it can be readily converted to the corresponding boronic acid by converting the halide compound to a lithium salt followed by treatment with a trialkoxy boron compound followed by acid. The same conversion can also be accomplished through catalytic borylation using a palladium-based catalyst. Specific examples for synthesizing compounds described herein are presented below in the Examples section.

Any of the compounds synthesized by the methods described herein can exist or be converted to the salt thereof. In one aspect, the salt is a pharmaceutically acceptable salt. The salts can be prepared by treating the free acid with an appropriate amount of a chemically or pharmaceutically acceptable base. Representative chemically or pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of the compound to base used is chosen to provide the ratio desired for any particular salts. For preparing, for example, the ammonium salts of the free acid starting material, the starting material can be treated with approximately one equivalent of base to yield a salt.

In another aspect, any of the compounds synthesized by the methods described herein can exist or be converted to the salt with a Lewis based thereof. The compounds herein can be treated with an appropriate amount of Lewis base. Representative Lewis bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, THF, ether, thiol reagent, alcohols, thiol ethers, carboxylates, phenolates, alkoxides, water, and the like. In one aspect, the reaction is conducted in water, alone or in combination with an inert, water-miscible organic solvent, at a temperature of from about 0° C. to about 100° C. such as at room temperature. The molar ratio of the compound to base used is chosen to provide the ratio desired for any particular complexes. For preparing, for example, the ammonium salts of the free acid starting material, the starting material can be treated with approximately one equivalent of chemically or pharmaceutically acceptable Lewis base to yield a complexe.

Ester derivatives are typically prepared as precursors to the carboxylic acid form of the compounds—as illustrated in the examples below—and accordingly can serve as precursors or prodrugs. Generally, these derivatives will be lower alkyl esters such as methyl, ethyl, and the like. Amide derivatives —(CO)NH$_2$, —(CO)NHR and —(CO)NR$_2$, where R is an alkyl group defined above, can be prepared by reaction of the carboxylic acid-containing compound with ammonia or a substituted amine.

Ether derivatives are typically prepared as precursors to the boronic acid form of the compounds—as illustrated in the examples below—and accordingly can serve as precursors or prodrugs. Generally, these derivatives are prepared by reactions with alcohols, or 1,2- or 1,3-diols.

b. Pharmaceutical Compositions

Any of the compounds synthesized by the methods described herein can be formulated into a pharmaceutical composition. In one aspect, a compound having the formula II can be combined with at least one pharmaceutically-acceptable carrier to produce a pharmaceutical composition. The pharmaceutical compositions can be prepared using techniques known in the art. In one aspect, the composition is prepared by admixing the compound with a pharmaceutically-acceptable carrier. The term "admixing" is defined as mixing the two components together. Depending upon the components to be admixed the components may or may not chemically or physically interact with one another.

Pharmaceutically-acceptable carriers are known to those skilled in the art. These most typically would be standard carriers for administration to humans, including solutions such as sterile water, saline, and buffered solutions at physiological pH.

Molecules intended for pharmaceutical delivery may be formulated in a pharmaceutical composition. Pharmaceutical compositions may include carriers, thickeners, diluents, buffers, preservatives, surface-active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally, applied to the skin, etc.).

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

It will be appreciated that the actual preferred amounts of active compound in a specified case will vary according to the specific compound being utilized, the particular compositions formulated, the mode of application, and the particular situs and mammal being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (2004).

c. Macromolecules Modified with Boronic Acid Fluorescent Compounds

Described herein are modified-macromolecules comprising a macromolecule having at least one compound having the formula II incorporated therein. It is contemplated that one or more of the compounds described herein can be incorporated into a macromolecule. The term "incorporated" as used herein refers to any chemical interaction that takes place when the macromolecule is mixed with the boronic acid compound. The chemical interaction can involve, for example, a covalent bond, and electrostatic interaction, hydrophobic interaction, or a hydrogen bond interaction. When the macromolecule and the boronic acid compound interact, a new (i.e., modified) macromolecule is produced.

The term "macromolecule" as used herein is any bioactive molecule that is capable of interacting with the boronic acid compound. Examples of macromolecules useful herein include, but are not limited to, an oligonucleotide, a nucleic acid or a metabolically stabilized analogue thereof, a polypeptide, a lipid, a dendrimer, a polymer, a glycoprotein, lipopolysaccharide, a glycolipid, or a pharmaceutically-acceptable compound. Techniques for incorporating the boronic acid compound into the macromolecule will vary depending upon the selection of the boronic acid compound and macromolecule.

II. Methods of Use and Articles

The boronic acid compounds and modified macromolecules described herein can be used to detect analytes.

In one aspect, described herein is a method for detecting an analyte, comprising (a) contacting the analyte with a compound having the formula II described above to produce a tagged analyte; and
(b) detecting the fluorescent emission produced from the tagged analyte.

In one aspect, described herein is a method for detecting an analyte, comprising (a) contacting the analyte with a modified macromolecule described herein to produce a tagged analyte; and
(b) detecting the fluorescent emission produced from the tagged analyte.

The first step involves contacting the analyte with one or more compounds having the formula II or modified macromolecules described herein. Upon contacting, the analyte interacts with the compound or modified macromolecule to produce a tagged analyte. The interaction between the compound or modified macromolecule and the analyte will vary depending upon the selection of the compound or modified macromolecule and the particular analyte to be detected. For example, the compound or modified macromolecule can form a covalent bond or an electrostatic interaction with the modified macromolecule to produce the tagged analyte.

After the contacting step, the fluorescent emission produced from the tagged analyte is detected. One advantage of the boronic acid compounds described herein is that once the boronic acid compound interacts with the analyte, the fluorescence produced by the tagged analyte is generally higher than the fluorescence emission from the original boronic acid compound. Not wishing to be bound by theory, it is believed that boronic acid compounds described herein undergo an apparent $pK_a$ change upon binding with the analyte. For example, the conversion of a phenylboronic acid analog to its ester with sugars commonly results in the lowering of the apparent $pK_a$ by about 2-3 pH units. Further, boronic ester formation frequently results in the conversion of the boron atom from the neutral $sp^2$ form to the anionic $sp^3$ form at physiological pH. Such a change can cause a change of hybridization status of the boron and consequently changes its electronic properties. This change in hybridization can be used to modulate the chromophoric properties of boronic acid compounds described herein in order to manipulate their electronic (i.e., fluorescent) properties.

The fluorescent emission produced by the tagged analyte can be detected using techniques known in the art such as, for example, a spectrofluorometer. The methods described herein can be used to qualitatively and quantitatively detect an analyte.

In one aspect, analyte comprises a natural or synthetic oligonucleotide, a natural or modified/blocked nucleotide/nucleoside, a nucleic acid (DNA) or (RNA), a peptide comprising natural or modified/blocked amino acid, an antibody, a parasite, a hapten, a biological ligand, a protein membrane, a lipid membrane, a small pharmaceutical molecule, a virus, a bacterium, or a cell. Below are several examples of analytes that can be detected using the techniques described herein.

Any type of cell can be an analyte. For example, eukaryotic cells and prokaryotic cells can be biomolecules. Examples of Eukaryotic cells that can be biomolecules are all types of animal cells, such as mammal cells, reptile cells, amphibian cells, and avian cells, blood cells, hepatic cells, kidney cells, skin cells, brain cells, bone cells, nerve cells, immune cells, lymphatic cells, brain cells, plant cells, and fungal cells. In another aspect, the biomolecule can be a component of a cell including, but not limited to, the nucleus, the nuclear membrane, leucoplasts, the microtrabecular lattice, endoplasmic reticulum, ribosomes, chromosomes, cell membrane, mitochondrion, nucleoli, lysosomes, the Golgi bodies, peroxisomes, or chloroplasts.

Any type of bacteria can be an analyte. Examples of bacterium include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chiamydia, Chlamydophila, Chromobacterium, Chyseobacterium, Chryseomonas, Citrobacter, Clostridium, Collinsella, Comamonas, Corynebacterium, Coxiella, Cryptobacterium, Delffia, Dernabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella.* Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies paratuberculosis, *Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides,* and other *Nocardia* species, *Streptococcus viridans* group, *Peptococcus* species, *Peptostreptococcus* species, *Actinomyces israelii* and other *Actinomyces* species, and *Propionibacterium acnes, Clostridium tetani, Clostridium botulinum,* other *Clostridium* species, *Pseudomonas aeruginosa,* other *Pseudomonas* species, *Campylobacter* species, *Vibrio cholerae, Ehrhchia* species, *Actinobacillus pleuropneumoniae, Pasteurella haemolytica, Pasteurella multocida,* other *Pasteurella* species, *Legionella pneumophila,* other *Legionella* species, *Salmonella typhi,* other *Salmonella* species, *Shigella* species *Brucella abortus,* other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi,* other *Hemophilus* species, *Yersinia pestis, Yersinia enterolitica,* other *Yersinia* species, *Escherichia coli, E. hirae* and other *Escherichia* species, as well as other *Enterobacteria, Brucella abortus* and other *Brucella* species, *Burkholderia cepacia, Burkholderia pseudomallei, Francisella tularensis, Bacteroides fragilis, Fudobascterium nucleatum, Provetella* species, and *Cowdria ruminantium,* or any strain or variant thereof.

Any type of virus can be an analyte. Examples of viruses include, but are not limited to, Herpes simplex virus type-1, Herpes simplex virus type-2, Cytomegalovirus, Epstein-Barr virus, Varicella-zoster virus, Human herpesvirus 6, Human herpesvirus 7, Human herpesvirus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency cirus, Human T-cell Leukemia virus type-1, Hantavirus, Rubella virus, Simian Immunodeficiency virus, Human Immunodeficiency virus type-1, Vaccinia virus, SARS virus, and Human Immunodeficiency virus type-2, or any strain or variant thereof.

Any type of parasite can be an analyte. Examples of parasites include, but are not limited to, *Toxoplasma gondii, Plasmodium falciparum, Plasmodium vivax, Plasmodium malariae*, other *Plasmodium* species, *Trypanosoma brucei, Trypanosoma cruzi, Leishmania* major, other *Leishmania* species, *Schistosoma mansoni*, other *Schistosoma* species, and *Entamoeba histolytica*, or any strain or variant thereof.

Any type of protein can be an analyte. For example, the protein can include peptides or fragments of proteins or peptides. The protein can be of any length, and can include one or more amino acids or variants thereof. The protein(s) can be fragmented, such as by protease digestion, prior to analysis. A protein sample to be analyzed can also be subjected to fractionation or separation to reduce the complexity of the samples. Fragmentation and fractionation can also be used together in the same assay. Such fragmentation and fractionation can simplify and extend the analysis of the proteins.

Any type of antibody can be an analyte. As used herein, the term "antibody" encompasses, but is not limited to, whole immunoglobulin (i.e., an intact antibody) of any class, chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. For example, fragments of antibodies which maintain binding activity are included. Such antibodies and fragments can be made by techniques known in the art. Methods for producing antibodies and screening antibodies for specificity and activity (See Harlow and Lane. Antibodies, A Laboratory Manual. Cold Spring Harbor Publications, New York, (1988)). The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof. Also included within the meaning of "antibody" are conjugates of antibody fragments and antigen binding proteins (single chain antibodies) as described, for example, in U.S. Pat. No. 4,704,692, the contents of which are hereby incorporated by reference.

Any type of antigen can be an analyte. "Antigen" as used herein includes substances that upon administration are capable of eliciting an immune response, thereby stimulating the production and release of antibodies that bind specifically to the antigen. Antigens include molecules and/or moieties that are bound specifically by an antibody to form an antigen/antibody complex. Examples of antigens include, but are not limited to, peptides, polypeptides, proteins, nucleic acids, DNA, RNA, saccharides, combinations thereof, fractions thereof, or mimetics thereof.

In one aspect, the analyte is a nucleic acid. Nucleic acids such as deoxyribonucleic acid (DNA), ribonucleic acid (RNA), and peptide nucleic acid (PNA) are polymeric, polyionic molecules soluble in aqueous solution under certain conditions. The assumed three-dimensional structures of nucleic acids in solution as a function of pH, ionic strength, counter ions, charge neutralization, hydration, organic precipitants, molecular composition, etc., are known by those skilled in the art. In one aspect, the nucleic acid can be single or double stranded DNA or RNA. In one aspect, the biomolecule comprises an oligonucleotide having from about 5 to about 500 nucleotides, about 5 to about 200 nucleotides, or from about 10 to about 100 nucleotides.

In another aspect, the analyte is a carbohydrate. Examples of carbohydrates that can be detected include, but are not limited to, fructose, galactose, glucose, mannose, arabinose, sorbitol, tagatose, lactose, fucose, sialyl Lewis X, sialyl Lewis a, Lewis Y, Lewis X, blood group antigens, and other oligosaccharide that are part of glycoproteins, glycolipids, lipopolysaccharides, stage specific antigens, cancer carbohydrate-containing biomarkers. Not wishing to be bound by theory, it is believed that the cis-1,2- or 1,3-diols of saccharides form five- or six-membered rings with boronic acid. As discussed above, the spectroscopic properties of boronic acid change when boron is hybridized from a $sp^2$ to $sp^3$ hybridization state. Thus, the compounds and compositions described herein have numerous applications with respect to recognizing sugars such as, for example, the blood sugar of a subject.

The methods described herein have numerous in vivo and in vitro applications with respect to diagnostics, therapeutics, and research tools. For example, the administration of the boronic acid compounds or modified macromolecules described herein to a subject can be used as imaging agents for the detection of certain analytes. In one aspect, boronic acid compounds or their modified forms can bind to cell-surface carbohydrates and initiate biological processes such as apoptosis. Such binding may also prevent viral fusion to host cells and block viral infection. They can also bind to bacterial surface carbohydrates as part of the lipopolysaccharides and prevent bacterial attachment to host tissues. Such boronic acids immobilized on a solid-phase material can also be used as implanted sensors for the continous monitoring of blood glucose concentrations.

Alternatively, the detection methods can be performed in vitro. In one aspect, an article can be coated with one or more boronic acid compounds or modified macromolecules described herein and the resulting article can be used as a diagnostic. For example, a sensory ship or microplate can be coated with the compositions described herein. These can be used (1) for the detection of lipopolysaccharides of bacterial origin, (2) for the determination of glucose concentration in monitoring the glucose level of diabetic patients or others who may have a need to monitor their glucose levels or (3) for the detection of glycoproteins such as the prostate-specific antigen (PSA).

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

A. Procedures for the Fluorescence Binding Studies

1. General Methods

2-Benzothienylboronic acid (BTBA) (Compound 5, Table 1) and sugars were purchased from Aldrich and used as received. The water used for the binding studies was double distilled and further purified with a Milli-Q filtration system. A Shimadzu RF-5301PC fluorometer was used for all fluorescent studies. Quartz cuvettes were used in all studies.

2. Fluorescence Binding Studies

For a typical sugar-BTBA fluorescent measurement, a $1.0 \times 10^{-5}$ M stock solution of BTBA in 0.10 M phosphate buffer at pH 7.4 was made as solution A. The sugar was added to a portion of solution A to make a $1.0 \times 10^{-5}$ M BTBA, $1.0 \times 10^{-3}$ M sugar solution as solution B. Solution B was titrated into solution A in order to make mixtures with a constant concentration of BTBA and a range of concentrations of the sugar. Each mixture was allowed to stand for at least 10 min, then 3.0 mL of the mixture was transferred into a cuvette for fluorescence measurement.

B. Calculation Method of Association Constants (Ka)

The association constants (Ka) were determined according to the method III in Valeur's publication (*J. Phys. Chem.* 1988, 92, 6233).

$$I_F^0/(I_F - I_F^0) = [a/(b-a)][(1/Ka[M]) + 1]$$

As shown in the above equation, when $1/(I_F - I_F^0)$ is plotted against the reciprocal of the sugar concentration [M$^{-1}$], the associate constant is given by the ratio of intercept/slope. Using this method, we calculated all the binding constants according to the sugar titration data. All the data was plotted on Microsoft Excel and showed excellent linear relationship ($R^2 > 0.99$).

C. Results

The effect of different sugars on the fluorescent properties of compound 5 (Table 1) was determined in phosphate buffer at pH 7.4. The fluorescence spectral changes of 5 with fructose at different concentrations are shown in FIG. 1. In the absence of fructose, compound 5 displayed two emission bands at 305 and 334 nm, respectively. With the addition of fructose, the fluorescence spectrum of 5 showed an increase in emission intensity at 305 nm while a decrease in intensity occured at 334 nm. This dual emission nature of compound 5 could be used for ratiometric sensing. More interesting, compound 5 displayed a new emission band at 317 nm upon addition of fructose with the disappearance of peak at 334 nm.

Figure 2:
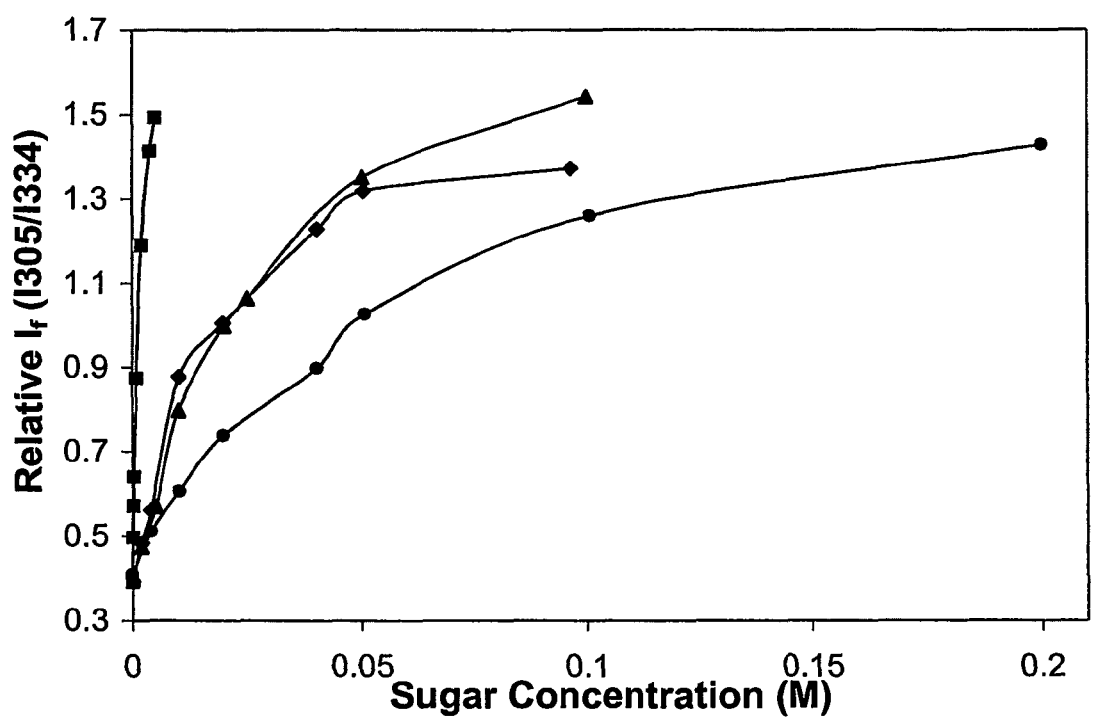
FIG. 2 shows the relative fluorescence intensity of 5 ($1 \times 10^{-5}$ M; Table 1) in 0.10 M phosphate buffer at pH 7.4 in the presence of D-fructose (■), D-galactose (▲), D-mannose (♦), and D-glucose (●): $\lambda_{ex}$=274 nm, $\lambda_{em}$=305 and 334 nm.

In an effort to examine the generality of this phenomenon, a few other sugars were tested (FIG. 2). All sugars tested were found to provide the same dual emission spectra as that of fructose at physiological pH. Fructose induced the largest fluorescence intensity ratio (305/334) increase. The binding constants (Ka) between compound 5 and the four sugars were further determined assuming the formation of a 1:1 complex (Table 2) (Fery-Forgues, S.; Le Bris, M.-T.; Guette, J.-P.; Valeur, B. *J. Phys. Chem.* 1988, 92, 62336237).

It is worth mentioning here that the order and absolute numbers of affinity of compound 5 are different from those of simple phenylboronic acid. For example, phenylboronic acid has a smaller Ka of 5 M$^{-1}$ for glucose compared to that of galactose (15 M$^{-1}$) (Springsteen, G.; Wang, B. *Tetrahedron* 2002, 58, 5291̄5300).

Compound 5, on the other hand, has a larger Ka for glucose (27 M$^{-1}$) than galactose (19 M$^{-1}$). However, it is not readily clear why this compound should have a different trend in its binding with various sugars as compared to other monoboronic acids.

TABLE 2

Association constants (Ka) of 5 with different sugars

| Sugar | $K_a$ (M$^{-1}$) |
|---|---|
| fructose | 656 ± 28 |
| galactose | 19 ± 0.7 |
| mannose | 30 ± 1.4 |
| glucose | 27 ± 4.9 |

Figure 3:
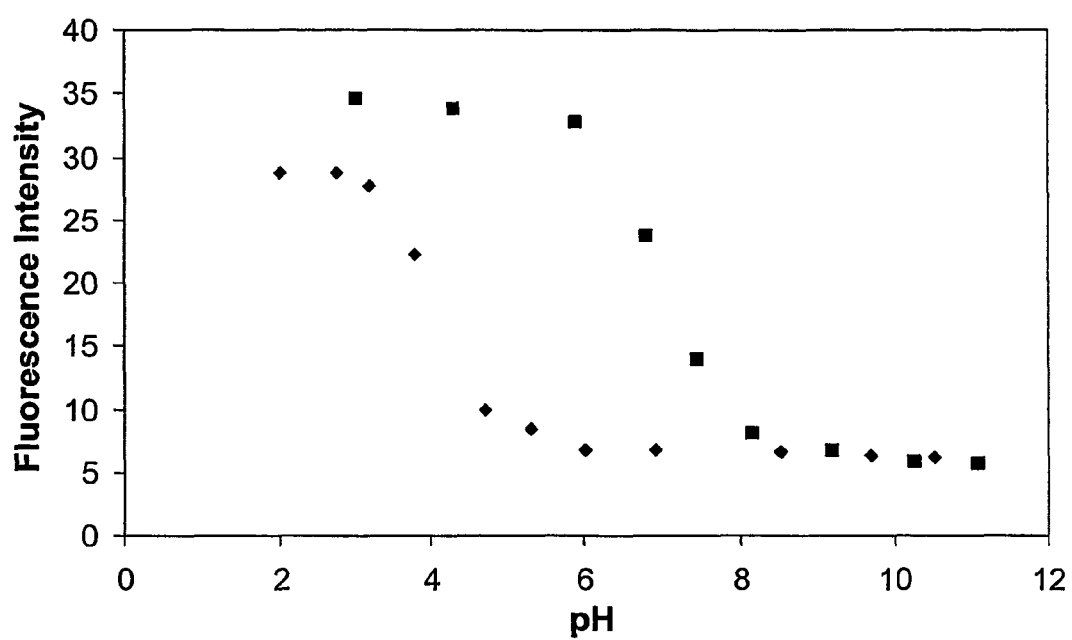
FIG. 3 shows the fluorescence intensity pH profile of 5 ($1 \times 10^{-5}$ M; Table 1) in 0.10 M phosphate buffer: [saccharide]= 0.5 M, $\lambda_{ex}$=274 nm, $\lambda_{ex}$=334 nm. ■1, ▼1+0.5 M D-fructose.

Since the fluorescence intensity increase upon binding with a sugar seems to be a general phenomenon, the fluorescence change mechanism of compound 5 at pH 7.4 was investigated. For this purpose, the fluorescence pH profiles of both compound 5 alone and compound 5 in the presence of fructose (0.5 M) were studied. The fluorescence intensity of 5 at 334 nm in the absence of sugars decreased upon changing the pH from 3 to 12 (FIG. 3). An apparent pKa of 7.0 was observed, which is assigned to the boronic acid moiety. The fluorescence intensity of 5 at 334 nm in the presence of fructose also decreased upon changing the pH from 2 to 11 and a pKa at 4.0 was observed. It is well-known that the binding of a diol to boronic acid often lowers the pKa of the boron species) (Springsteen, G.; Wang, B. *Tetrahedron* 2002, 58, 5291-5300). Therefore, the pKa, which drops from 7.0 to 4.0, can also be reasonably assigned to boron. These results indicate that the boronic acid moiety of compound 5 in the presence and absence of fructose exists predominantly in the anionic tetrahedral form at pH 7.4. It seems that the fluorescence intensity change of compound 5 is also due to diol's perturbation as that of 8-quinolineboronic acid. This indicates that the new mechanism of fluorescence intensity change found on 8-quinolineboronic acid is not limited to quinoline-type compounds, other types of heterocyclic system may also have the same property.

In summary, compound 5 was found to be a new type of fluorescent reporter compound with many desirable properties for biosensor preparation. Such properties include (1) dual fluorescence suitable for ratiometric sensing and (2) being functional in aqueous solution at physiological pH. Moreover, it shows an unusual dual emission upon binding with a sugar. To the best of our knowledge, this represents the first example of dual fluorescence carbohydrate sensor with an emission band shift.

Example 2

Compound 1 (Table 1) was readily synthesized from the commercially available 1-bromo-4-(dimethylamino)naphthalene through lithiation and reaction with trimethylborate (Scheme 1). Purification of the crude product by silica gel chromatography and recrystalization from dichloromethane-hexanes afforded 1 as a colorless crystal. Selected characterization data for 4-(dimethylamino)-naphthalene boronic acid (1): colorless crystal, yield 42%; HRESI-MS: Calcd. for $C_{12}H_{15}BNO_2$ 216.1196 (M+H)$^+$, Found 216.1187; $^1$H NMR (400 MHz, $CD_3OD$) δ 2.87 (s, 6H), 7.10 (d, J=7.2, 1H), 7.45 (m, 3H), 7.76 (m, 1H), 8.21 (m, 1H); $^{13}$C NMR (400 MHz, $CD_3OD$) δ 113.23, 124.39, 124.68, 125.71, 128.45, 128.52, 130.48; Anal. Calcd for $C_{12}H_{14}BNO_2$-¾$H_2O$: C, 71.51, H, 6.25, N, 6.95; Found: C, 71.80, H, 6.42, N, 6.65.

Scheme 1

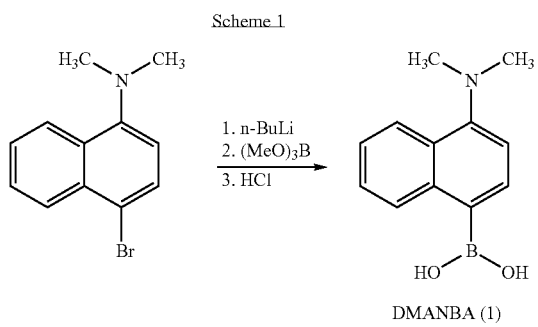

DMANBA (1)

Figure 4:
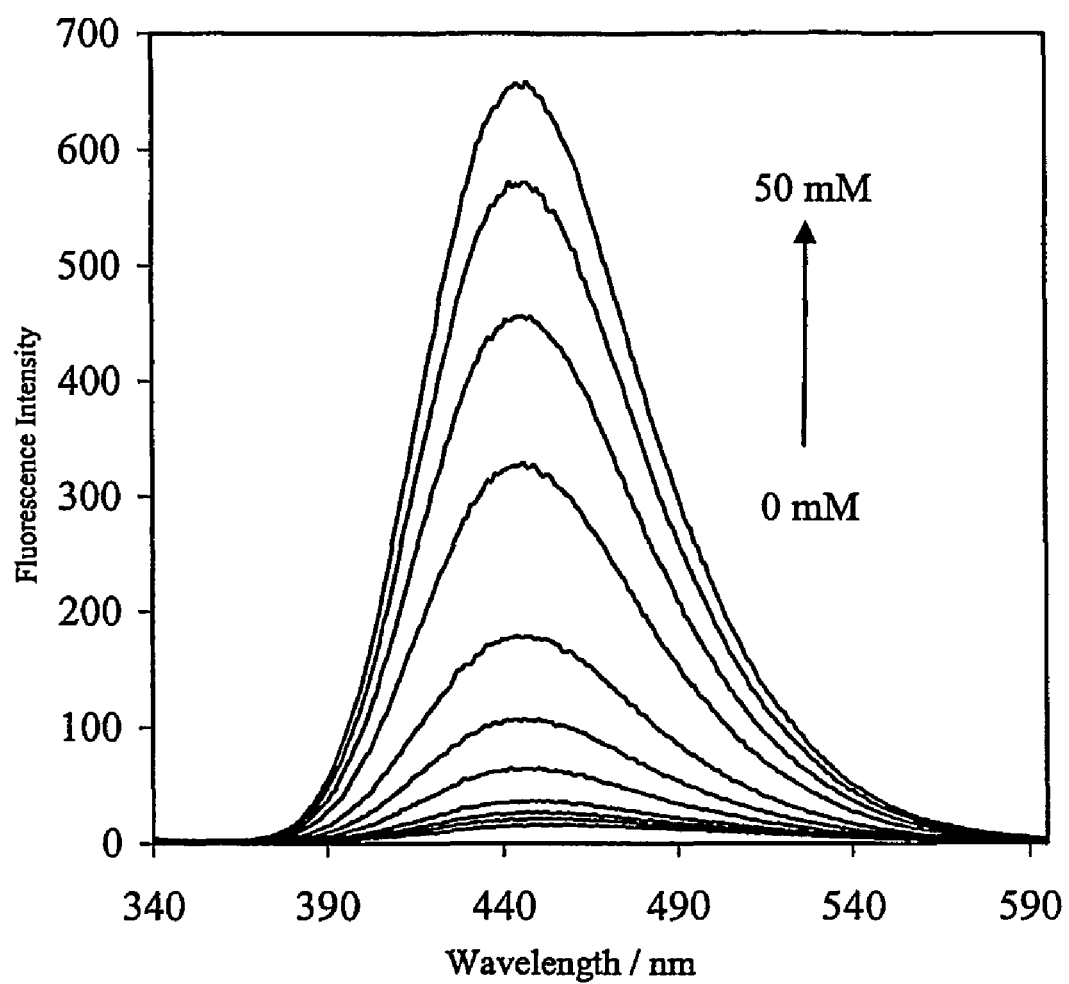
FIG. 4 shows the fluorescence spectral change of 1 ($1.0 \times 10^{-5}$ M) (Table 1) with different concentrations of D-fructose (0-50 mM) in 0.1 M aqueous phosphate buffer at pH 7.4, $\lambda_{ex}$=300 nm.

The effect of various carbohydrates on the fluorescent properties of compound 1 was determined in phosphate buffer at pH 7.4. The emission spectral change of 1 with fructose at different concentrations in 0.1 M aqueous phosphate buffer (pH 7.4) is shown in FIG. 4. A 41-fold emission intensity increase is observed in presence of 50 mM fructose. To the best of our knowledge, such a large emission intensity increase has never been reported for boronic acid-based saccharide sensors involving the ICT mechanism. The quantum yields of 1 in the absence ($\phi_F$=0.010) and in the presence of 50 mM fructose ($\phi_F$=0.42) in 0.1 M phosphate buffer (pH 7.4) were obtained using 8-quinoline boronic acid ($\phi_F$=0.58 in 12 M $H_2SO_4$) as a reference compound. Such results indicate that indeed addition of a carbohydrate result in a very significant change in the spectroscopic properties of the sensor compound (1).

Figure 5:
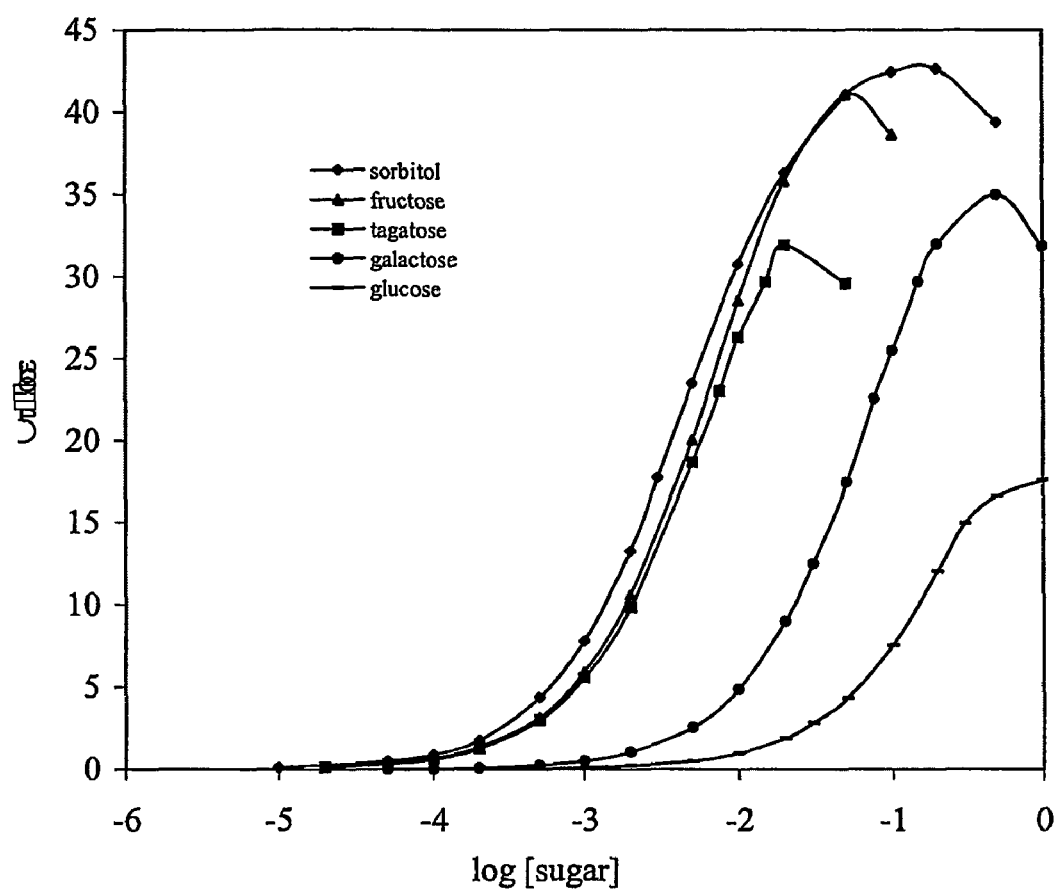
FIG. 5 shows the fluorescence intensity changes ($\Delta I/I_0$) of 1 ($1.0 \times 10^{-5}$ M in 0.1 M aqueous phosphate buffer at pH 7.4) (Table 1) as a function of sugar concentrations at 25° C.; $\lambda_{ex}$=300 nm, $\lambda_{em}$=445 nm.

To examine the general applicability of this fluorescent reporter compound, the effect of four other carbohydrates on its fluorescence intensity was investigated (FIG. 5). These carbohydrates include sorbitol, tagatose, galactose, and glucose. From FIG. 5, it is clear that all five carbohydrates tested caused significant fluorescence intensity increases at physiological pH with varying magnitude. Addition of sorbitol and fructose induced the largest fluorescence intensity changes, more than 40-fold, at concentrations above 50 mM. Glucose, on the other hand, induced a maximum of 17-fold fluorescence intensity increase at a much higher concentration (1 M).

To examine the binding in a more quantitative fashion, the association constants ($K_a$) between 1 and the five carbohydrates were determined assuming the formation of a 1:1 complex. As expected, the affinity trend with 1 followed that of simple phenylboronic acid in the order of sorbitol>fructose>tagatose>galactose>glucose (Table 3). The absolute numbers are also similar to what was observed with phenylboronic acid. For example, phenylboronic acid (PBA) has a $K_a$ of 162 $M^{-1}$ for fructose and 5 $M^{-1}$ for glucose.

TABLE 3

Association constants ($K_a$) and fluorescence intensity changes ($\Delta I/I_0$) of 1 with different sugars.

| sugar | $K_a$ ($M^{-1}$) | $\Delta I/I_0$ (sugar concentration, M) |
|---|---|---|
| sorbitol | 226 ± 5 | 42 (0.10) |
| fructose | 207 ± 4 | 41 (0.05) |
| tagatose | 116 ± 2 | 32 (0.02) |
| galactose | 12.0 ± 0.2 | 35 (0.50) |
| glucose | 4.0 ± 0.1 | 17 (1.0) |

Figure 6:
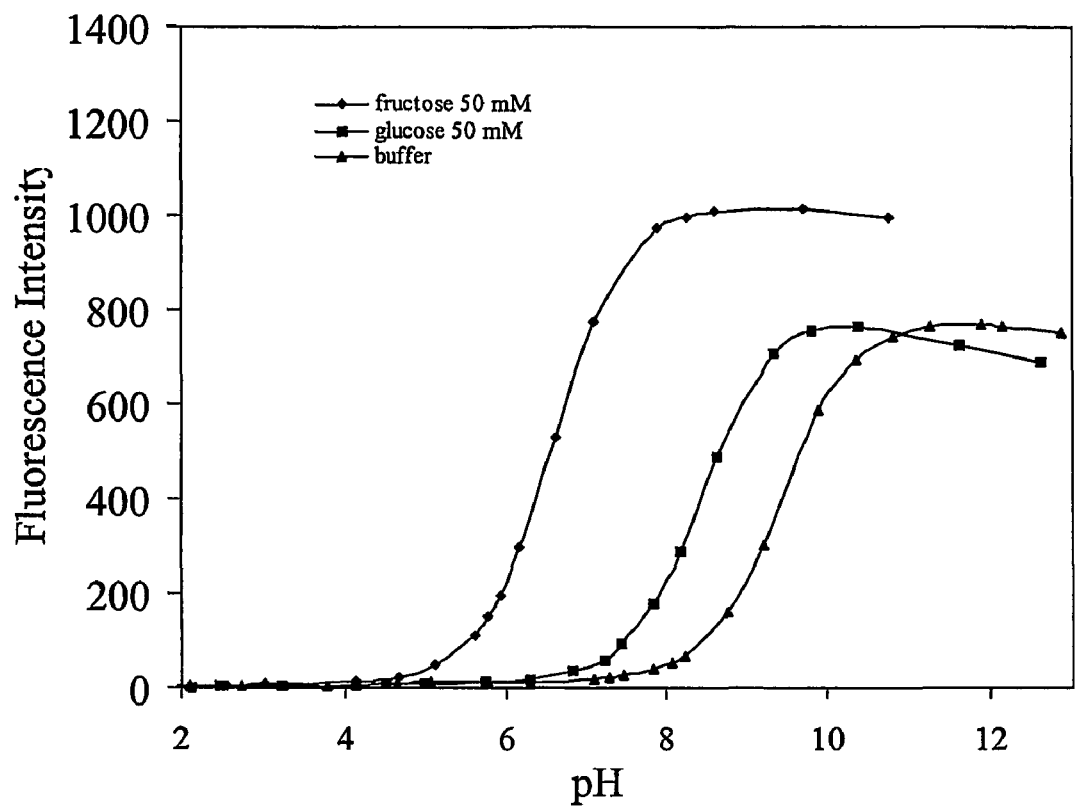
FIG. 6 shows the pH titration of the fluorescence intensity of 1 ($1 \times 10^{-5}$ M) (Table 1) in the absence and presence of sugars in 0.1 M aqueous phosphate buffer, $\lambda_{ex}$=300 nm, $\lambda_{em}$=445 nm.

To examine the relationship between the fluorescence intensity changes and the boron ionization states, the pH profile of the fluorescence intensity in the absence and presence of fructose and glucose at a fixed concentration (50 mM) was also studied (FIG. 6). The emission intensity of 1 in the absence of any carbohydrate increased by 168-fold at 445 nm upon changing the pH from 3 to 12. It is worth mentioning that the $pK_a$ of the protonated dimethyl amino group of 1 is about and the emission wavelength of 1 with the protonated dimethyl amino group at low pH is about 238 nm. Therefore, the fluorescence intensity of 1 at 445 nm was not affected by the protonated dimethyl amino group. The fluorescence intensity changes correspond to the boronic acid $pK_a$ (9.4) and therefore hybridization changes, which was responsible for the fluorescence intensity changes observed.

The pH titration curves of 1 in the presence of fructose and glucose showed over 140-fold increases in fluorescence intensity when pH increased from 3 to 10 (FIG. 6). It is well known that the binding of a diol to boronic acid most of the time lowers the $pK_a$ of the boron species. In our case, an apparent $pK_a$ of 6.4 was observed in the presence of 50 mM of fructose. As described earlier, the boronic acid moiety of 1 has a $pK_a$ of about 9.4. Therefore, at physiological pH, it exists in the neutral, non-ionized form. However, upon addition of fructose, the apparent $pK_a$ of the solution drops to about 6.4, which ensures that most of the boron species are in the anionic tetrahedral state at physiological pH. It should be noted that the pKa here is the apparent pKa because of the tridentate binding mode of fructose with a boronic acid.

The apparent $pK_a$ of the mixture of 1 and glucose (50 mM) was much higher (8.3) (FIG. 6). However, it should be noted that in this mixture only a small portion of the boronic acid is expected to be in the ester state because of the low association constant (4 $M^{-1}$), which gives about 20% complexation at pH 7.4. Therefore, this $pK_a$ is a reflection of a mixture of mostly the free boronic acid and a small portion of the ester.

Figure 7:
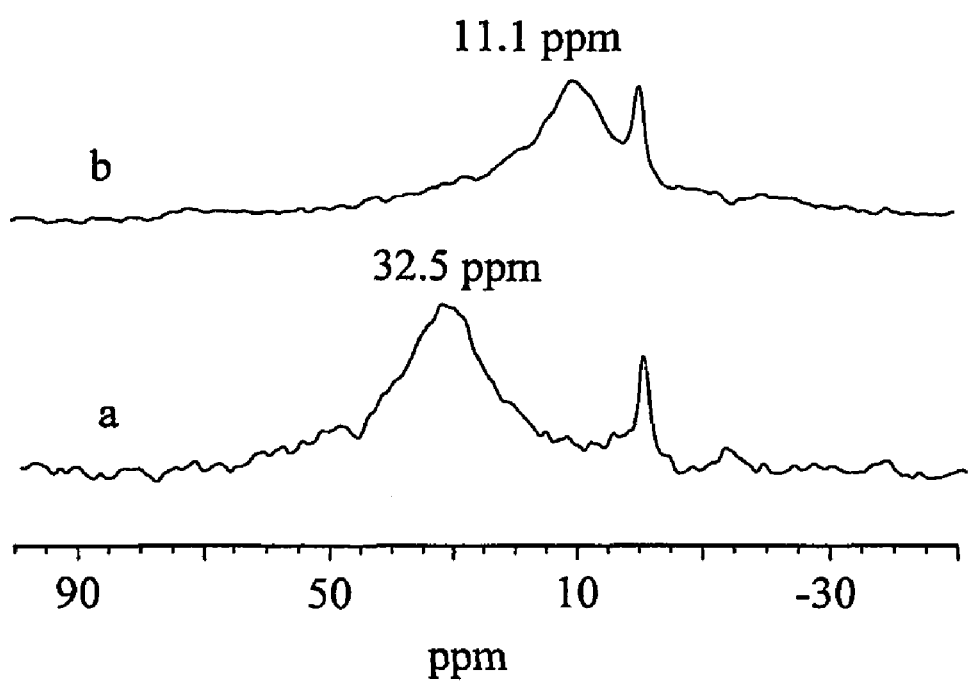
FIG. 7 shows the $^{11}$B NMR in DMSO/0.1 M aqueous phosphate buffer (1:3, pH 7.4). a: 1 (9 mM) alone; b: the mixture of 1 (9 mM) (Table 1) and fructose (20 eq., 0.18 M). BF$_3$ was used as an external reference.

In order to confirm the correlation of the fluorescence intensity increase of 1 with the ionization state change of the boronic acid, the $^{11}B$ NMR spectra of 1 in the absence and presence of fructose was recorded. The $^{11}B$ chemical shift of 1 changed from 32.5 ppm in the absence of fructose, which is characteristic of the neutral trigonal form of boronic acid, to 11.1 ppm in the presence of fructose (20 equivalents), which is characteristic of the anionic tetrahedron form of boronic acid (FIG. 7). Such $^{11}B$ NMR spectra results are consistent with the pH-fluorescence intensity titration results.

Example 3

Figure 8:
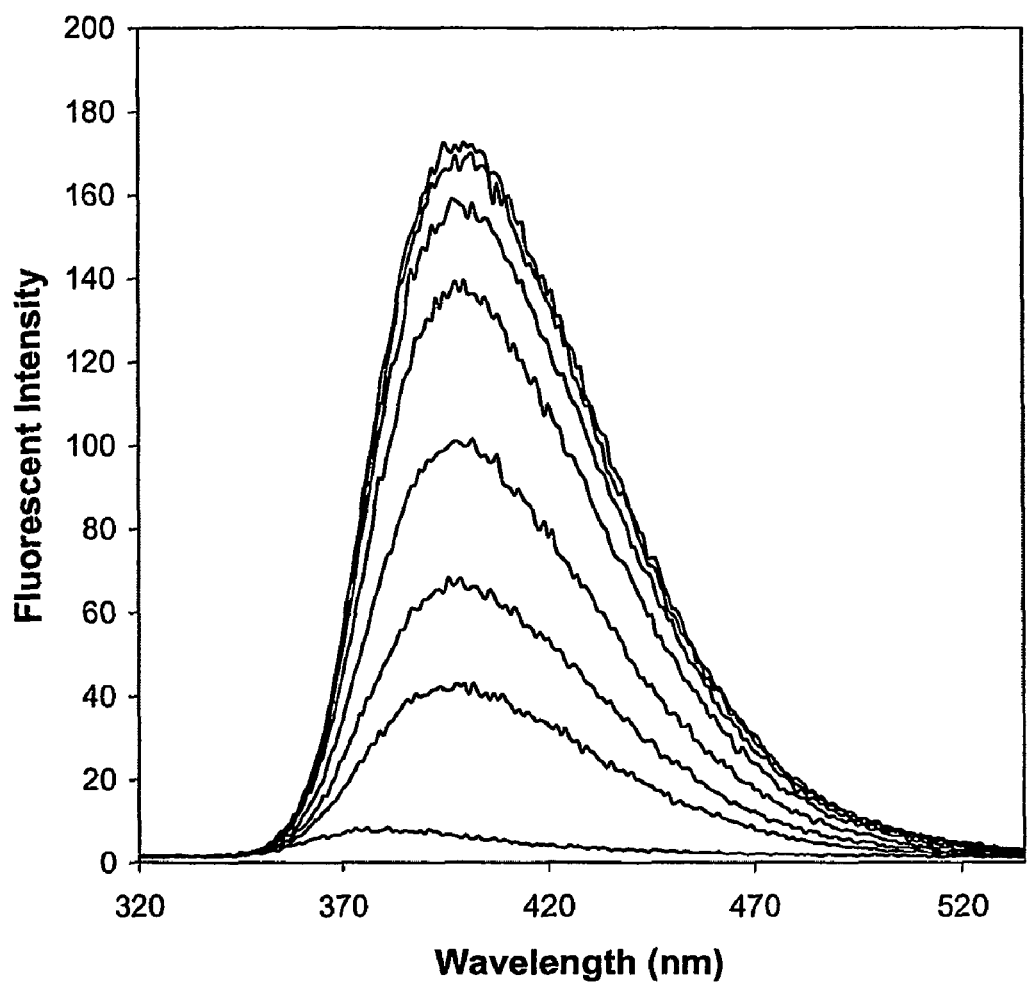
FIG. 8 shows the fluorescence response of 6 ($2 \times 10^{-5}$ M) (Table 1) in 0.10 M phosphate buffer at pH 7.4 in the presence of D-fructose (0, 0.5, 1.0, 2.0, 5.0, 10, 20, 25 mM): $\lambda_{ex}$=270 nm.
Figure 9:
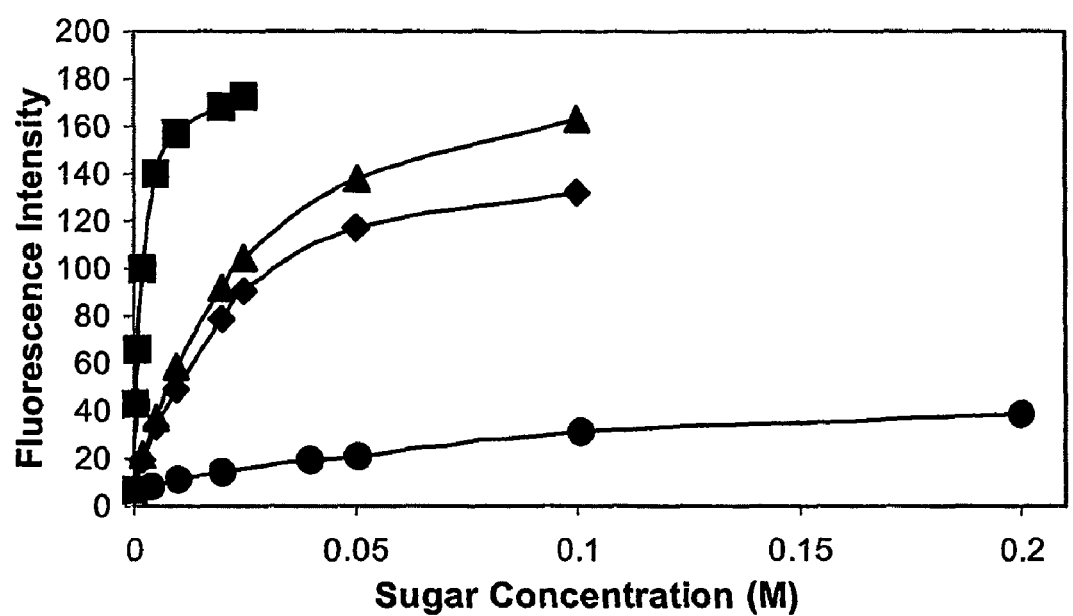
FIG. 9 shows the fluorescence intensity of 6 ($2 \times 10^{-5}$ M) (Table 1) in 0.10 M phosphate buffer at pH 7.4 in the presence of D-fructose (■), D-galactose (▲), D-mannose (♦), and D-glucose (●): $\lambda_{ex}$=270 nm, $\lambda_{em}$=400 nm.

The effect of different sugars on the fluorescent properties of compound 6 (Table 1) was determined in phosphate buffer at pH 7.4. The fluorescence spectral changes of 6 with fructose at different concentrations are shown in FIG. 8. A 25-fold emission intensity increase was observed in the presence of 25 mM fructose. This was accompanied by a 24 nm shift in the emission $\lambda_{max}$. In an effort to examine the generality of this phenomenon, a few other sugars were tested (FIG. 9). All sugars tested were found to cause significant fluorescence intensity increases at physiological pH with varying magnitude. Fructose induced the largest fluorescence intensity changes, about 25-fold, at a concentration of 25 mM. Glucose, on the other hand, induced a maximum of 6-fold fluorescence intensity increase at a higher concentration of 0.2 M. The binding constants (Ka) between compound 6 and the four sugars were further determined assuming the formation of a 1:1 complex. As expected, the affinity trend with 6 followed that of simple phenylboronic acid in the order of fructose>mannose≈galactose>glucose (Table 4).

TABLE 4

Association constants (Ka) and fluorescence intensity
changes ($\Delta I/I_0$) of 1 with different sugars

| Sugar | Ka (M$^{-1}$) | $\Delta I/I_0$ (sugar concentration, M) |
|---|---|---|
| Fructose | 544 ± 22 | 25 (0.025) |
| Galactose | 46 ± 9 | 16 (0.025) |
| Mannose | 48 ± 5 | 14 (0.025) |
| Glucose | 5.1 ± 1.0 | 6 (0.20) |

Figure 10:
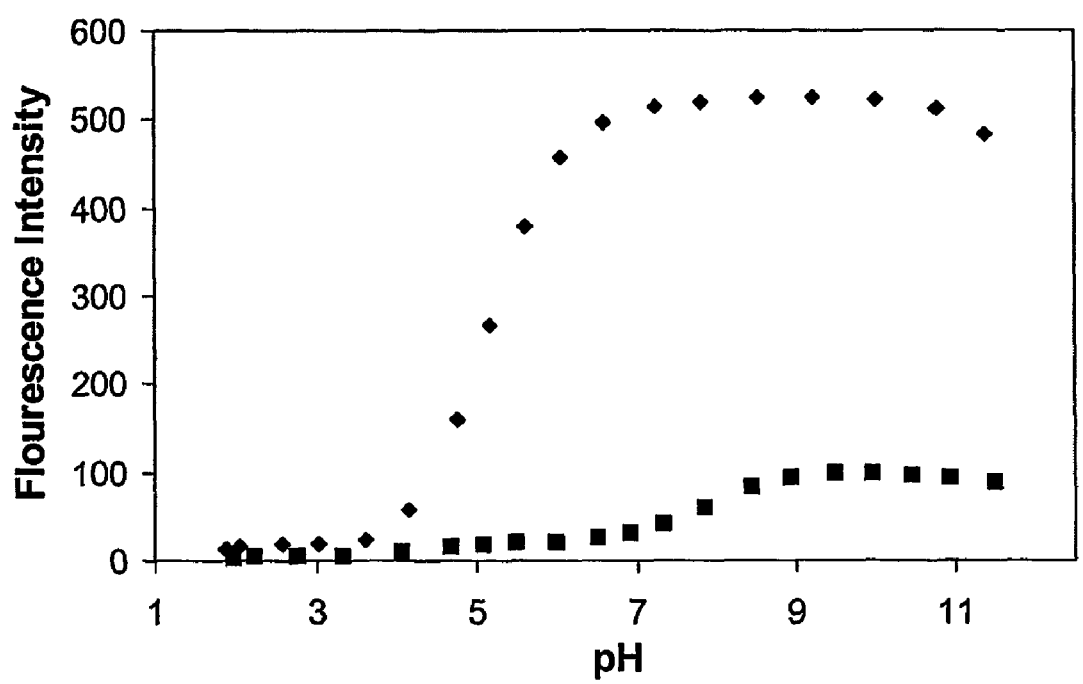
FIG. 10 shows the fluorescence intensity pH profile of 1 ($2\times10^{-5}$ M) in 0.10 M phosphate buffer: [saccharide]=0.5 M, $\lambda_{ex}$=270 nm, $\lambda_{em}$=400 nm. ■1, ◆1+0.5 M D-fructose.

Since the fluorescence intensity increase upon binding with a sugar seems to be a general phenomenon, next the conditions under which optimal fluorescence intensity changes are observed upon addition of a sugar was investigated. For this purpose, the fluorescence pH profiles of both compound 6 alone and in the presence of fructose (0.5 M) were studied. The fluorescence intensity of 6 in the absence of sugars increased by 17-fold upon changing the pH from 3 to 12 (FIG. 10). An apparent pKa of 7.9 was observed, which is assigned to the boronic acid moiety. Since the pKa of phenylboronic acid is 8.8 and electron-withdrawing groups are known to lower the pKa of a boronic acid, it is reasonable to expect that pKa of the boronic acid moiety in 6 to be less than 8.8. Furthermore, one would expect the pKa values of the other two ionizable groups, the carboxylic acid and the quinolinium groups, to be less than 7. Therefore, assigning the pKa at 7.9 to the boronic acid moiety is the most reasonable option. The fluorescence intensity of 6 in the presence of fructose increased by 35-fold upon changing the pH from 2 to 10 and a pKa at 5.2 was observed. It is well-known that the binding of a diol to boronic acid often lowers the pKa of the boron species. Therefore, the pKa, which drops from 7.9 to 5.2, can also be reasonably assigned to boron. These results indicate that the boronic acid moiety of compound 6 exists at pH 7.4 predominantly in the neutral, non-ionized form. Upon addition of fructose, the pKa of the boron drops to about 5.2, which ensures that most of the boron species are in the anionic tetrahedral state at physiological pH. Such titration results also mean that the ionization states of the other two ionizable functional groups, quinoline and carboxylic acid, do not seem to affect the fluorescence intensity of 6.

It is worth mentioning that the fluorescence intensity increase of compound 6 upon binding with sugars is observable in the whole range of pH above 5.0. This suggests that 6 could be used for monitoring sugar at any pH value in the range. Particularly important is that 6 shows close to optimal fluorescence intensity changes at physiological pH. As with the free boronic acid, the most fluorescent form in the presence of fructose is the form when the boron is in the anionic tetrahedral form.

The finding of compound 6 as a new fluorescent sensor with a boronic acid group that is not directly attached to the quinoline moiety indicates that the quinoline moiety could be used as a general fluorescent reporter for carbohydrate sensor development. Furthermore, 6 has a free carboxylic acid, which can be used as a handle for tethering other functional groups.

Example 4

Figure 11:
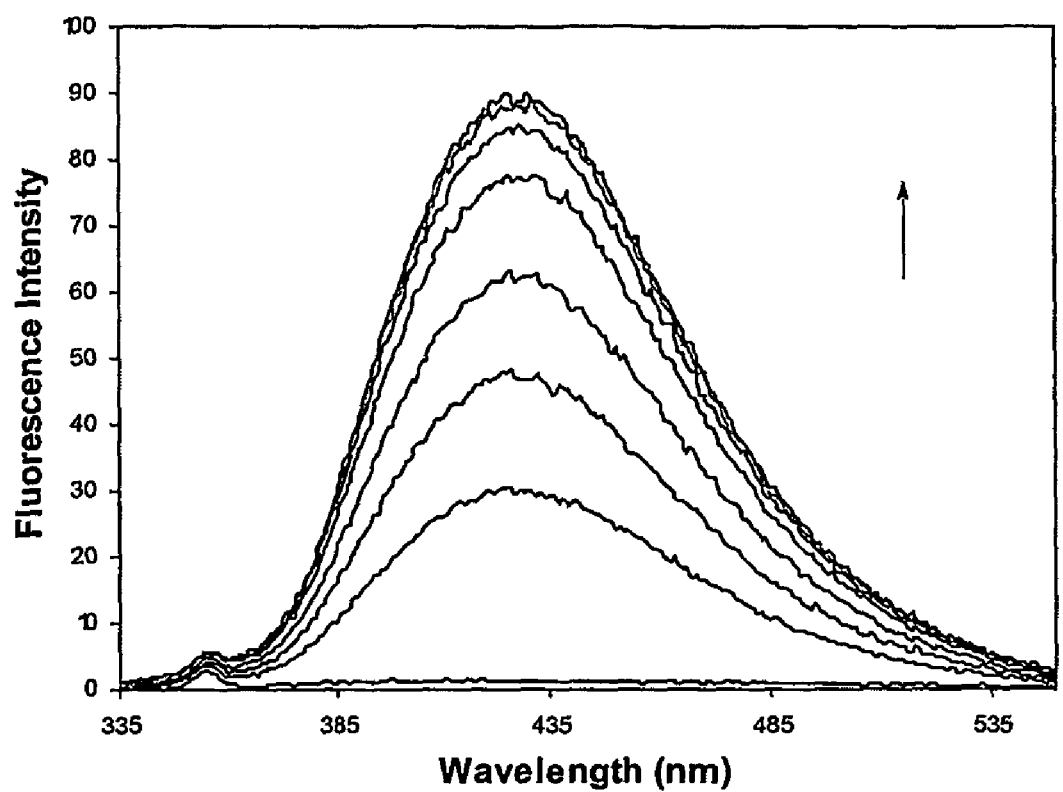
FIG. 11 shows the fluorescence spectra of 5-QBA (5.8× $10^{-5}$ M) upon addition of D-fructose (0, 0.5, 1.0, 2.0, 5.0, 10, 20, 50 mM) in 0.1 M phosphate buffer at pH 7.4: $\lambda_{ex}$=315 nm.
Figure 12:
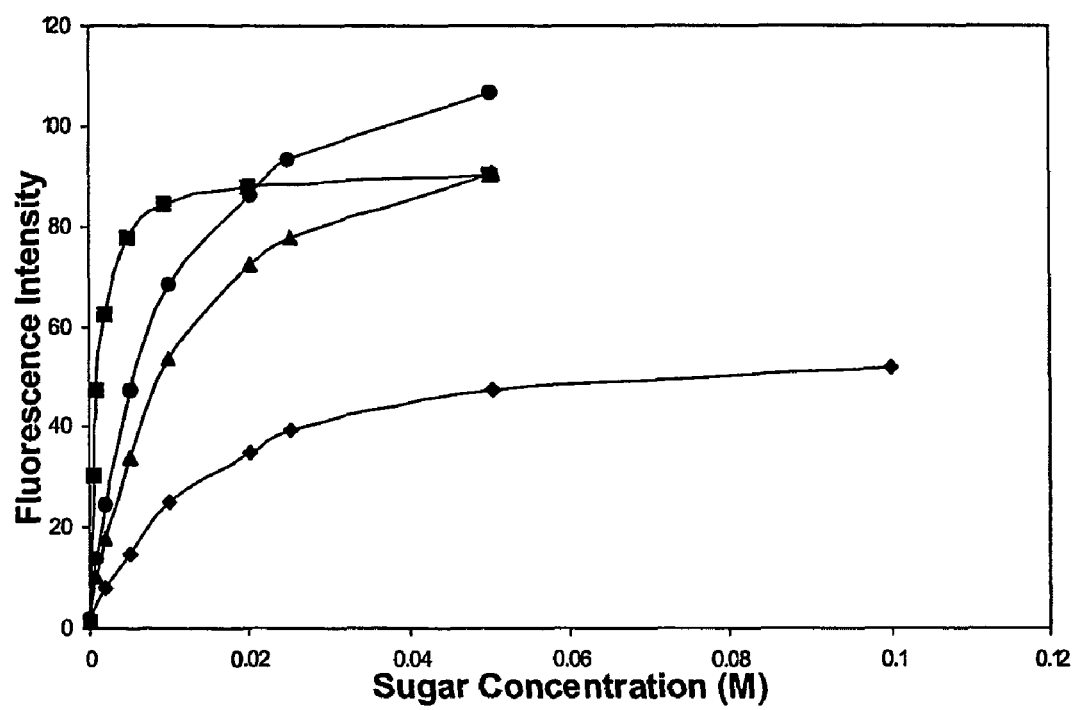
FIG. 12 shows the fluorescence intensity of 5-QBA (5.8× $10^{-5}$ M) in 0.10 M phosphate buffer at pH 7.4 in the presence of D-fructose (■), D-galactose (▲), D-mannose (◆), and L-arabinose (●): $_{ex}$=315 nm, $\lambda_{em}$=425 nm.

5-QBA (compound 3 in Table 1) itself is essentially non-fluorescent at pH above 5 and weakly fluorescent at lower pH in aqueous solution. However, upon addition of D-fructose, the fluorescence intensity increased dramatically in a concentration-dependent manner (FIG. 11). In an effort to examine the generality of this phenomenon, a few other sugars were tested. FIG. 12 shows the concentration profiles of fructose, arabinose, galactose, and mannose with binding constants of 924±88 M$^{-1}$, 121±16 M$^{-1}$, 90±2 M$^{-1}$, and 60±2 M$^{-1}$, respectively. It is interesting to point out that the binding constants of 5-QBA with different monosaccharides are significantly higher compared to 8-QBA (compound 4 in Table 1). For example, the binding constant of 5-QBA with D-fructose is increased by more than 8 folds compared with that of 8-QBA.

Figure 13:
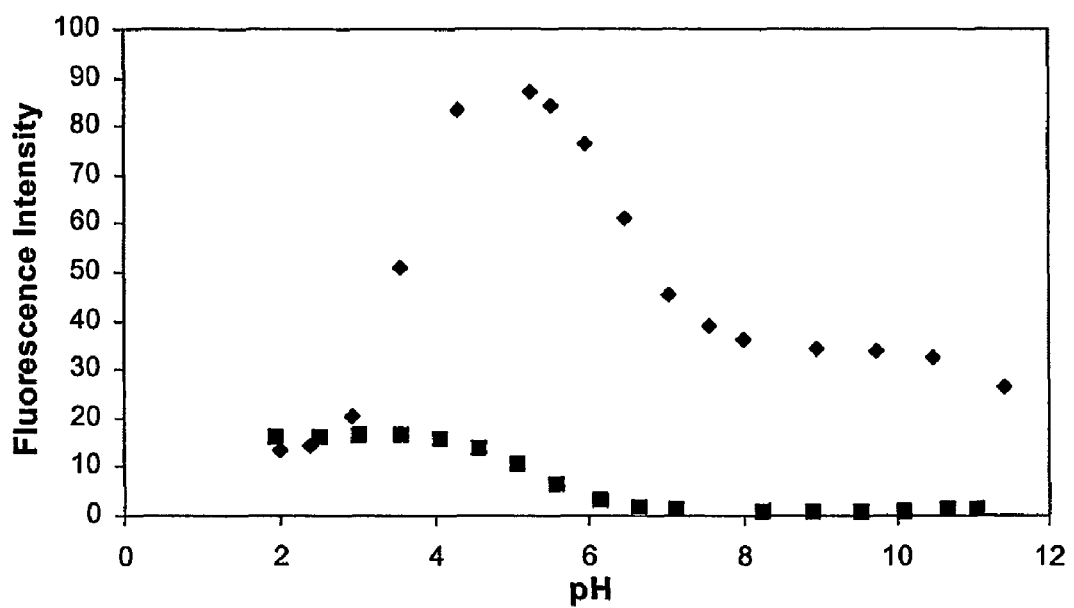
FIG. 13 shows the fluorescence intensity pH profile of 5-QBA (5.8×$10^{-5}$ M) in 0.10 M phosphate buffer: $\lambda_{ex}$=315 nm, $\lambda_{em}$=425 nm. ■5-QBA, ◆5-QBA+0.5 M D-fructose.

Since the fluorescence intensity increase upon binding with a sugar seems to be a general phenomenon, the use of 5-QBA functions as a fluorescent probe for diols was investigated. The fluorescence pH profiles of both 5-QBA alone and 5-QBA in the presence of D-fructose (0.5 M) were investigated. Based on the fluorescence intensity changes, only one pKa at 5.2 was observed for 5-QBA in the absence of a sugar and two pKa's at 3.5 and 6.6 were observed in the presence of fructose (FIG. 13). The UV pH titration of 5-QBA and its ester did not provide useful information for the pKa determination. In order to assign each pKa, the $^{11}$B NMR spectra of 5-QBA and its ester in a mixed deuterated methanol-water (1:1) solvent at different pH were obtained. Methanol was used so that the concentration of 5-QBA can be increased to 57 mM so as to allow for a meaningful NMR determination within a reasonable period of time.

It should be noted that the addition of 50% methanol to water solution results in minimal changes of the solution pH. The boron signal of 5-QBA appeared at 30.0 ppm at both pH 2.0 and 7.0, consistent with the neutral trigonal boron. At an increased pH (7.5), two boron signals at 30.0 and 10.0 ppm were observed indicating a mixture of both the neutral and anionic species. In this case, the appearance of two peaks at pH 7.5 indicated that the inter-conversion between the anionic and neutral species must be sufficiently slow with 5-QBA so that the two ionization states can be observed individually. At pH 12, a single peak at 5.7 ppm was found indicating the presence of only the anionic tetrahedral state. These results indicated that the boron of the free acid changed hybridization from sp$^2$ to sp$^3$ between pH 7.0 to 12. Thus, the first pKa of 5-QBA at 5.2 was assigned to the quinolinium nitrogen, and the second pKa corresponding to boronic acid ionization must be between pH 7.0 and 12. This pKa assignment is opposite to that of 8-QBA. For the fructose ester of 5-QBA, we observed the same chemical shifts (at about 10.5 ppm) at pH 6.0 and 11. This clearly indicated that the boron in the ester did not change hybridization state between pH 6.0 to 11. Therefore, it is reasonable to assign that first pKa at 3.5 to the boronic ester group, and the second pKa at 6.6 to the quinolinium nitrogen. Such results indicate that the pKa of the boronic acid is higher in the absence of a sugar, but lower in the presence of a sugar than that of the quinolinium nitrogen. Such a pKa-switching seems to correspond to the highest fluorescence intensity change at pH 5.8 (FIG. 13).

The availability of water-soluble fluorescent reporter compounds such as 5-QBA will significantly help the effort of making biocompatible fluorescent sensors for macromolecules such as, for example, cell-surface carbohydrates biomarkers.

Example 5

Compound 7 in Table 1

A. Experimental

5-Nitro-1-bromonaphthalene (A). A mixture of 1-nitronaphthalene (10.0 g, 58 mmol) and FeCl$_3$ (0.066 g, 0.41 mmol) was heated to 90° C. To the solution was added dropwise bromine (3.0 mL, 58 mmol) (no any solvent was used for this reaction). The reaction mixture was stirred at 90° C. for 2 hrs. After cooling down to room temperature, the mixture was recrystallized from ethanol to give compound A as a yellow needle crystal (7.3 g, 50%). mp 119-120° C.; $^1$H NMR (300 MHz, CDCl$_3$) δ 8.44 (d, J=8.7 Hz, 1H), 8.34 (d, J=8.7 Hz, 1H), 8.13 (d, J=7.5 Hz, 1H), 7.81 (d, J=7.5 Hz, 1H), 7.56 (t, J=8.1 Hz, 1H), 7.44 (t, J=8.1 Hz, 1H); $^{13}$C NMR (75 MHz, CDCl$_3$) δ 147.2, 133.6, 132.7, 131.8, 129.6, 126.4, 125.7, 124.6, 123.7, 123.0. EI-MS (m/z) Calcd. for C$_{10}$H$_6$BrNO$_2$: 251 (M$^+$), Found: 251.

5-Amino-1-bromonaphthalene (B). To the solution of 5-nitro-1-bromonaphthalene (A) (2.5 g, 10 mmol) in EtOH/AcOH /Dioxane/H$_2$O (2:2:2:1) (30 mL) was added Fe (5.6 g, 100 mmol) and 2 drops of 2 N HCl. The reaction mixture was stirred at 100° C. for 2 hrs. After evaporation of solvent, the residue was dissolved in 100 mL DCM and washed with 5% NaHCO$_3$ (3×30 mL) and dried over Na$_2$SO$_4$. After evaporation of solvent, the crude mixture was purified on a silica gel column, eluting with DCM/hexanes (1:1), to give compound B as a white powder (3.0 g, 97%). mp 65-66° C.; $^1$H NMR (400 MHz, CDCl$_3$) δ 7.79 (d, J=8.8 Hz, 1H), 7.76 (d, J=8.0, 1H), 7.71 (d, J=8.4 Hz, 1H), 7.39 (t, J=7.6 Hz, 1H), 7.28 (t, J=7.2 Hz, 1H), 6.83 (d, J=7.2 Hz, 1 H), 4.18 (s, 2H); $^{13}$C NMR (100 MHz, CDCl$_3$) δ 142.5, 133.0, 130.4, 128.0, 125.1, 125.0, 123.9, 121.0, 118.4, 110.9; ESI-MS (m/z) calcd. for C$_{10}$H$_9$BrN222.0 (M+H)$^+$, found 222.1. Anal. Calcd for C$_{10}$H$_8$BrN: C, 54.08; H, 3.63; N, 6.31. Found: C, 53.81; H, 3.46; N, 6.11.

5-(Dimethylamino)-1-bromonaphthalene (C). To the solution of 5-amino-1-bromonaphthalene (B) (0.8 g, 3.1 mmol) and CH$_3$I (1.9 mL, 31 mmol) in THF (50 mL) was added NaH (60%) (1.2 g, 31 mmol). The reaction mixture was stirred at 60° C. overnight. The precipitate was removed by filtration. After evaporation of solvent, the residue was dissolved in 100 mL DCM and washed with 5% NaHCO$_3$ (3×30 mL) and dried over Na$_2$SO$_4$. After evaporation of solvent, the crude compound was purified on a silica gel column, eluting with DCM/hexanes (1:3), to give compound C as a colorless oil (0.66 g, 85%). $^1$H NMR (300 MHz, CDCl$_3$) δ 8.43 (d, J=8.4 Hz, 1H), 8.06 (d, J=8.4 Hz, 1H), 7.82 (d, d, J=7.2, 1.2 Hz, 1H), 7.56 (t, d, J=7.5, 0.9 Hz, 1H), 7.41 (t, d, J=7.5, 0.9 Hz, 1H), 7.28 (d, d, J=7.2, 2.4 Hz, 1H), 3.02 (s, 6H); $^{13}$C NMR (75 MHz, CDCl$_3$) δ 151.5, 133.5, 130.5, 130.2, 127.5, 125.6, 124.5, 123.5, 122.1, 115.2, 45.7; ESI-MS (m/z) Calcd. for C$_{12}$H$_{13}$BrN:250.0 (M+H)$^+$, Found: 250.1.

5-(Dimethylamino)-naphthalene-1-boronic acid (compound 7 in Table 1). The solution of 5-(dimethylamino)-1-bromonaphthalene (C) (0.38 g, 1.5 mmol) in THF (5 mL) was cooled to −78° C. To the solution was added dropwise n-BuLi in hexanes (1.5 M) (1.4 mL, 2.1 mmol). The reaction mixture was stirred at −78° C. for 45 min and then (MeO)$_3$B (0.57 mL, 5.1 mmol) was added. After stirring at −78° C. for 1 hr, the temperature was warmed to room temperature and stirring was continued overnight. The solvent was removed in vacuum. The residue was dissolved in 100 mL DCM and washed with 0.5 N HCl (1×30 mL and 5% NaHCO$_3$ (3×30 mL) and dried over Na$_2$SO$_4$. After evaporation of solvent, the crude mixture was purified on a silica gel column, eluting with DCM/MeOH (20:1), to give compound 7 as a white powder (0.21 g, 65%). mp 95-96° C.; $^1$H NMR (300 MHz, CD$_3$OD) δ 8.25 (d, J=9.6, 1H), 7.48-7.43 (m, 3H), 7.38 (t, J=8.4, 1H), 7.09 (d, J=8.1, 0.6 1H), 2.94 (s, 6H); $^{13}$C NMR (75 MHz, CD$_3$OD) δ 151.4, 136.5, 129.8, 128.6, 125.9, 124.7, 124.4, 123.9, 113.9 44.58; HRESI-MS (m/z) Calcd. for C$_{12}$H$_{15}$BNO$_2$:216.1196 (M+H)$^+$, Found: 216.1196.

B. The Fluorescence Properties of 5-DMANBA (7)

Figure 14:
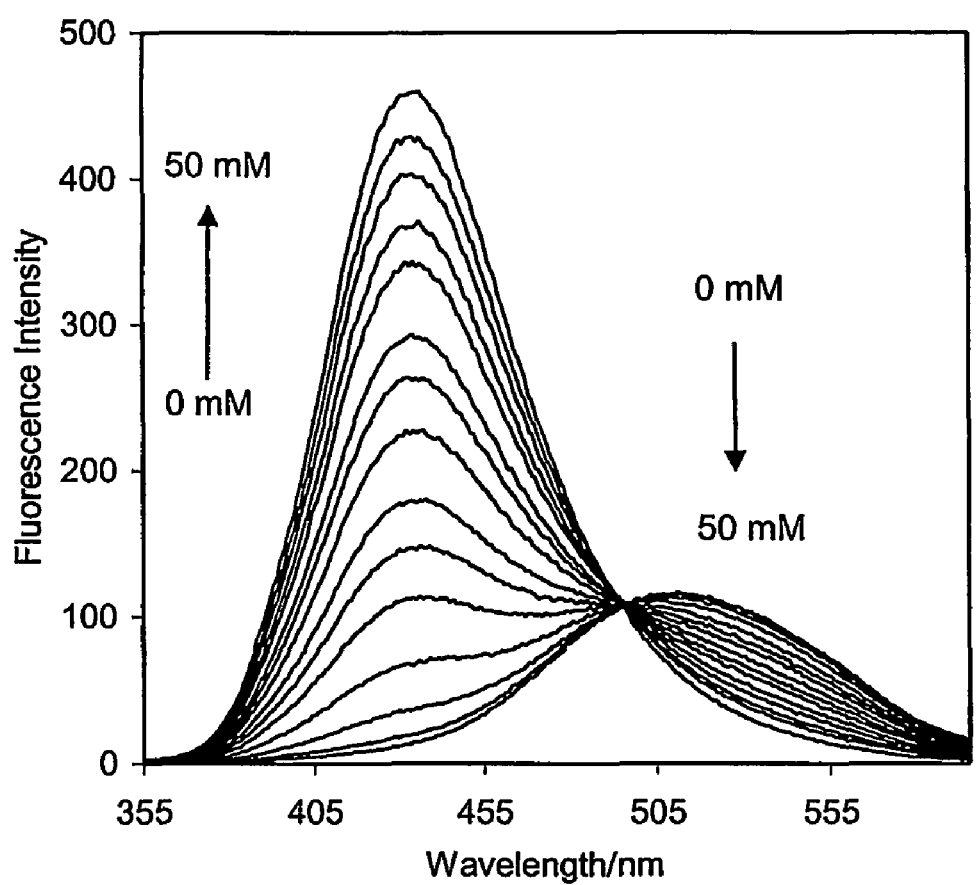
FIG. 14 shows the fluorescence spectral changes of 5-DMANBA (7) ($1.0\times10^{-5}$ M) with different concentrations of D-fructose (0-50 mM) in 0.1 M aqueous phosphate buffer at pH 7.4, $\lambda_{ex}$=300 nm.

5-DMANBA (7) exhibits an emission maximum of 513 nm (FIG. 14) and absorption maximum at 300 nm (FIG. 19B) in 0.1 M aqueous phosphate buffer at pH 7.4, with a Stokes shift of over 200 nm. Addition of a carbohydrate resulted in a significant decrease in fluorescence intensity at 513 nm and an even greater increase at 433 nm. For example, addition of fructose (50 mM) to the solution of 7 induced a 36-fold fluorescence intensity increase at 433 nm and a 0.55-fold fluorescence intensity decrease at 513 nm (FIG. 14). An isosbestic point was observed at 495 nm. To the best of our knowledge, such large emission intensity changes at two wavelengths have never been reported for boronic acid-based saccharide sensors. The quantum yields ($\phi_F$) of 7 were determined as 0.07 at 513 nm in 0.1 M phosphate buffer (pH 7.4) in the absence of a sugar and 0.23 at 433 nm in the presence of 50 mM of fructose, using 8-quinoline boronic acid ($\phi_F$=0.58 in 12 M H$_2$SO$_4$) as a reference compound.

Figure 15:
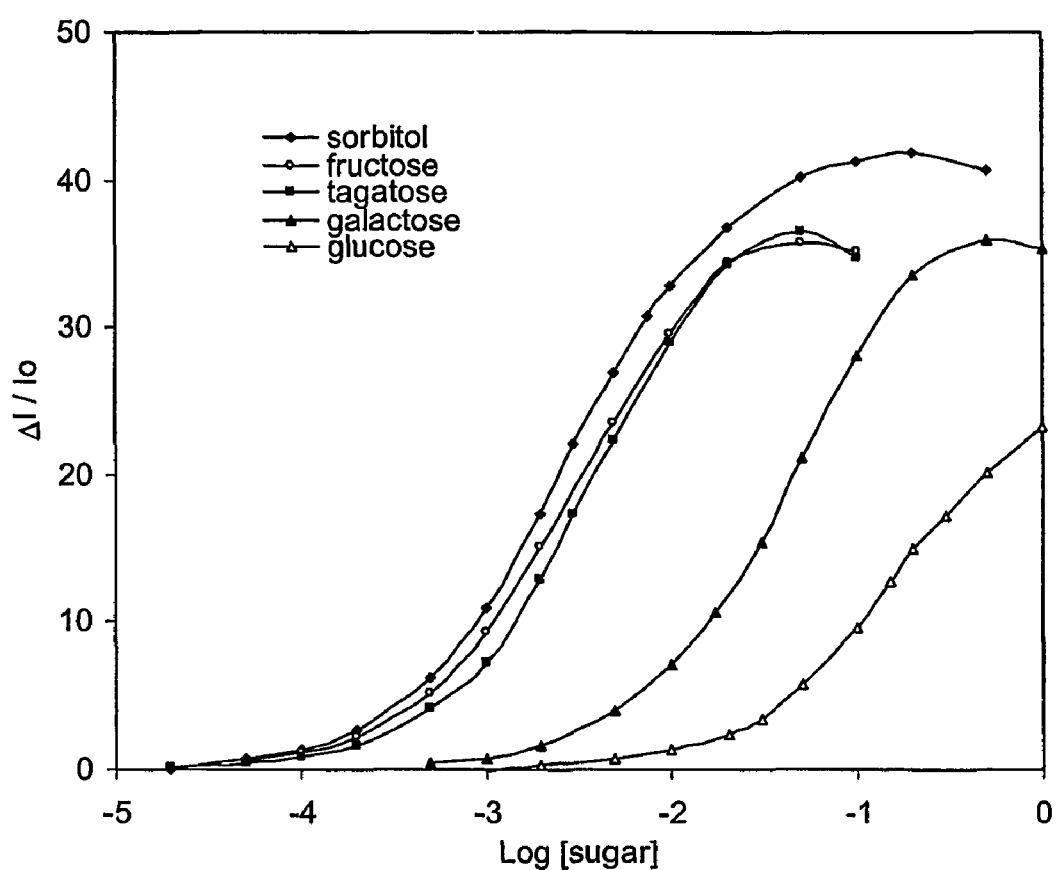
FIG. 15 shows the fluorescence intensity changes ($\Delta I/I_0$) of 5-DMANBA (7) as a function of sugar concentrations; $1.0\times10^{-5}$ M in 0.1 M aqueous phosphate buffer at pH 7.4; $\lambda_{ex}$=300 nm, $\lambda_{em}$=433 nm.
Figure 16:
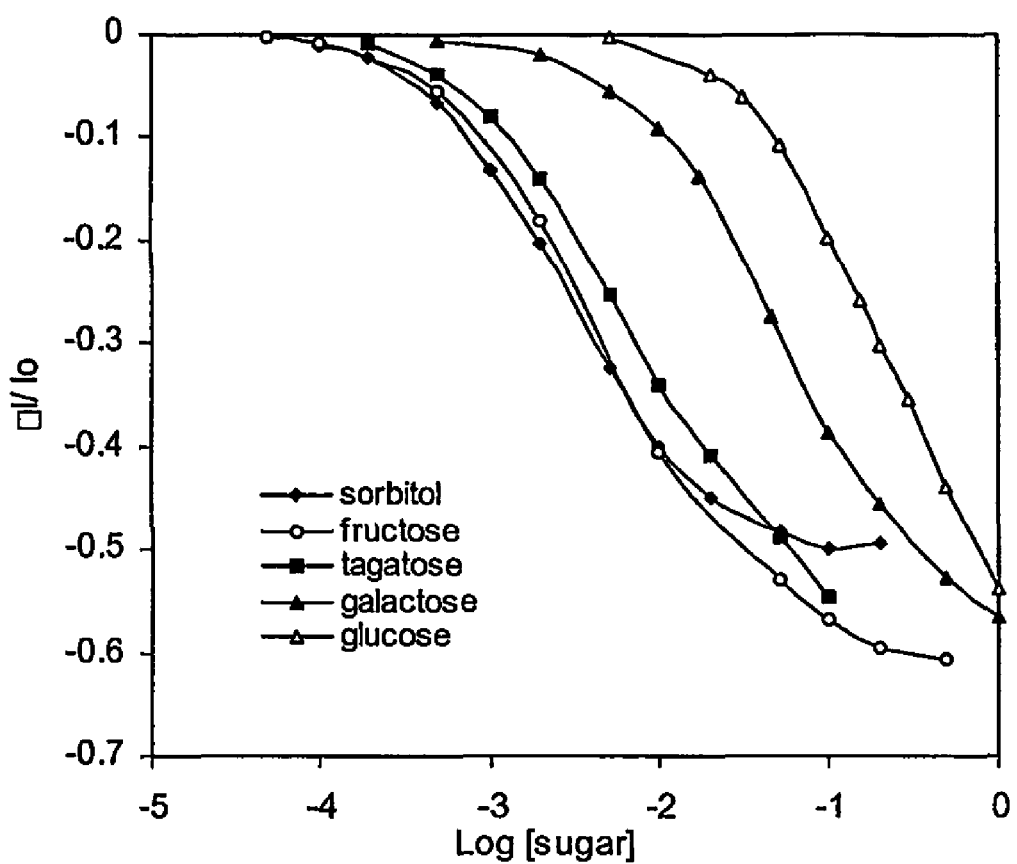
FIG. 16 shows the fluorescence intensity changes ($\Delta I/I_0$) of 5-DMANBA (7) as a function of sugar concentrations; $1.0\times10^{-5}$ M in 0.1 M aqueous phosphate buffer at pH 7.4; $\lambda_{ex}$=300 nm, $\lambda_{em}$=513 nm.

To examine the general applicability of this fluorescent reporter compound (7), the effect of four other carbohydrates on its fluorescence intensity was investigated (FIGS. 15 and 16). These carbohydrates include sorbitol, tagatose, galactose, and glucose. From FIG. 15, it is clear that all five carbohydrates tested caused a very large fluorescence intensity increase at 433 nm in aqueous solution at physiological pH with varying magnitude. Addition of sorbitol induced the largest fluorescence intensity increase (42-fold at 433 nm) at a concentration of 200 mM. Fructose, galactose, and tagatose induced about 36-fold increases in fluorescence intensity at 433 nm. Glucose, on the other hand, induced a maximum of 23-fold fluorescence intensity increase at 433 nm at a much higher concentration (1 M) (Table 5).

TABLE 5

Association constants ($K_a$) and fluorescence intensity changes ($\Delta I/I_0$) of 5-DMANBA (7) at 433 and 513 nm with different sugars.

| | | $\Delta I/I_0$ (sugar conc., M) | |
|---|---|---|---|
| sugar | $K_a$ (M$^{-1}$) | 433 nm | 513 nm |
| sorbitol | 337 ± 5 | 42 (0.20) | −0.48 (0.05) |
| fructose | 311 ± 4 | 36 (0.05) | −0.61 (0.05) |
| tagatose | 229 ± 3 | 37 (0.05) | −0.55 (0.05) |
| galactose | 23.0 ± 0.2 | 36 (0.50) | −0.56 (0.50) |
| glucose | 3.6 ± 0.1 | 23 (1.0) | −0.54 (1.0) |

FIG. 16 shows the effect of five carbohydrates on the fluorescence intensity property of 5-DMANBA at 513 nm. It is clear that all five carbohydrates tested caused a fluorescence intensity decrease at 513 nm in aqueous solution at physiological pH with varying magnitude ranging from 0.50- to 0.60-fold at different concentrations (Table 5).

Figure 17:
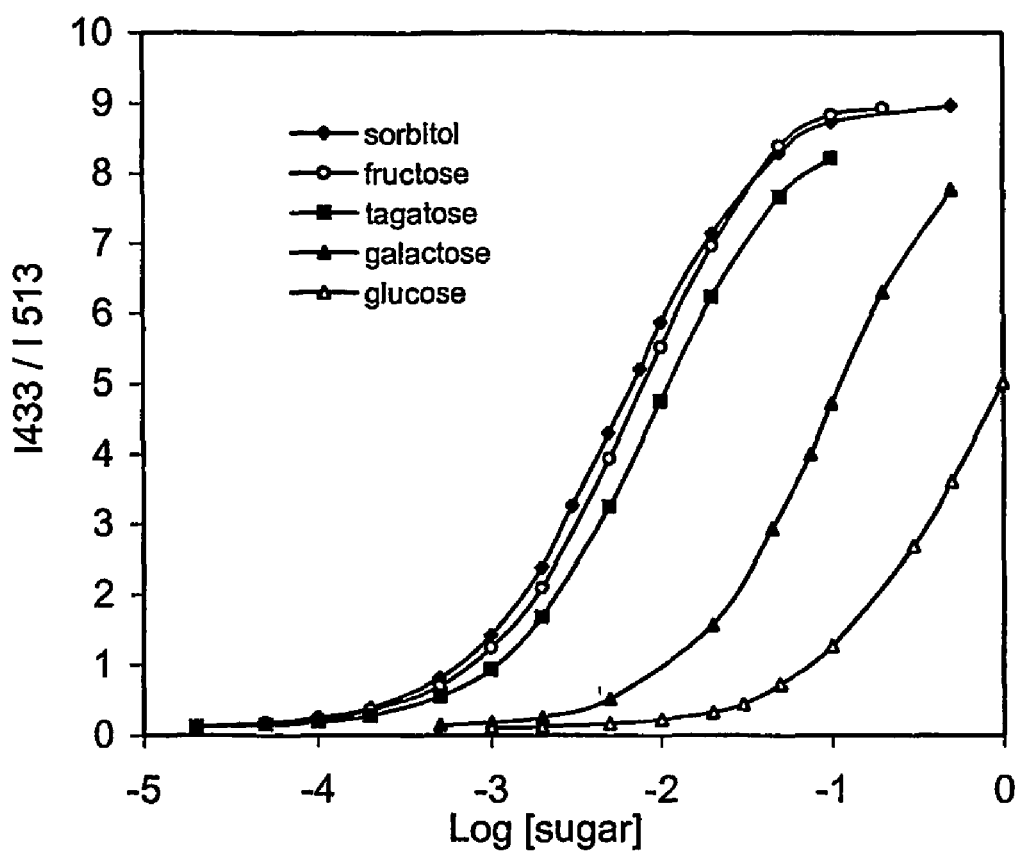
FIG. 17 shows the changes of the fluorescence intensity ratio of 5-DMANBA (7) ($I_{433}/I_{513}$) as a function of sugar concentrations; sensor concentration: $1.0\times10^{-5}$ M in 0.1 M aqueous phosphate buffer at pH 7.4; $\lambda_{ex}$=300 nm.

Because of the significant fluorescence intensity changes at two wavelengths in opposing directions, large changes in the emission intensity ratio at 433 and 513 nm ($I_{433}/I_{513}$) were observed upon addition of a sugar (sorbitol, fructose, tagatose, galactose, and glucose) to the solution of 7 (FIG. 17). For example, the ratio of the fluorescence intensity at 433 nm to that at 513 nm was 0.1:1 before addition of a sugar and 8.4:1 after addition of 50 mM fructose. This is a 84-fold change. A detectable fluorescence intensity ratio change can be observed upon addition of a low concentration of fructose. For example, emission intensity ratio at 433 and 513 nm ($I_{433}/I_{513}$) changed from 0.11 to 0.23 upon addition of 0.1 mM of fructose. The other carbohydrates also exhibited large changes in this ratio at different concentrations.

To examine the binding in a more quantitative fashion, the association constants ($K_a$) between 7 and five carbohydrates were determined assuming the formation of a 1:1 complex. As expected, the affinity trend of 7 followed that of simple monoboronic acid in the order of sorbitol>fructose>tagatose>galactose>glucose (Table 5). As expected, these binding constants are similar to what was observed with phenylboronic acid.

Figure 18:
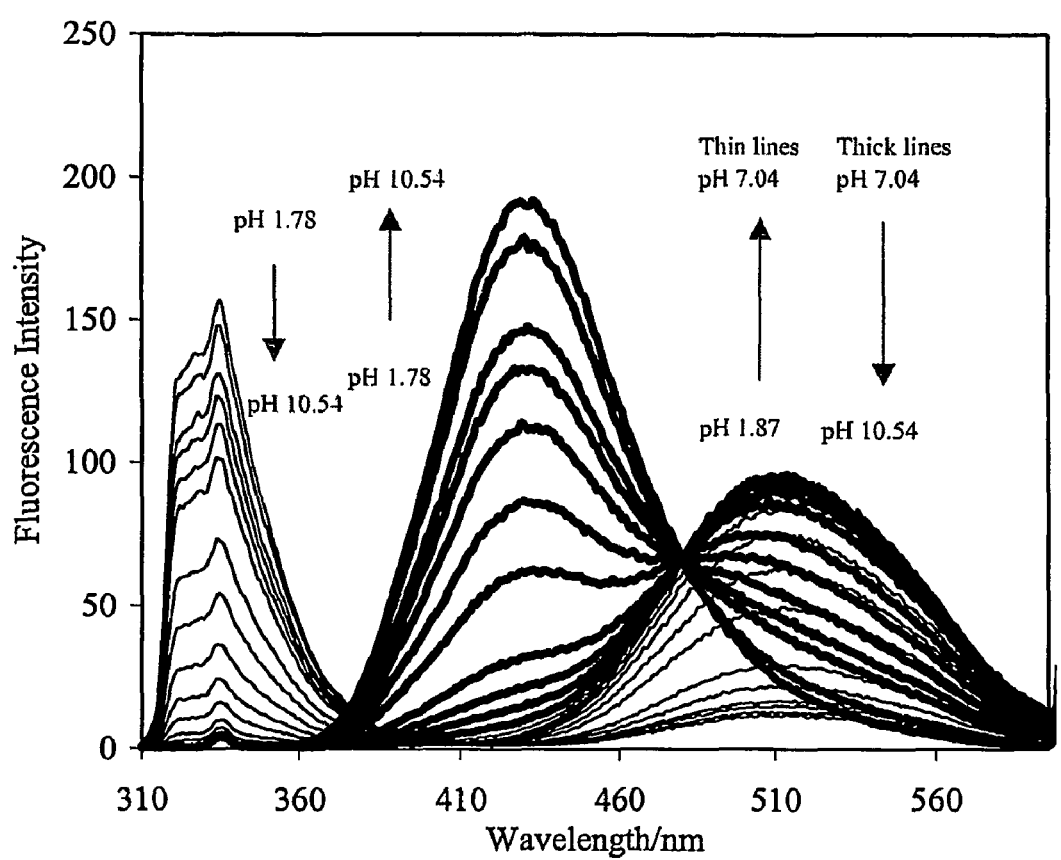
FIG. 18 shows the fluorescence spectral change of 5-DMANBA (7) ($1.0\times10^{-5}$ M) in the absence of sugar at different pH in 0.1 M aqueous phosphate buffer, $\lambda_{ex}$=300 nm.

To understand the structural features associated with the fluorescence intensity changes, we studied the pH profiles of the fluorescence intensity in the absence (FIG. 18) and presence of fructose and glucose at a fixed concentration (50 mM). A strong fluorescence peak at 335 nm and a weak fluorescence peak at 513 nm were observed at low pH (1.78) in the absence of a sugar (FIG. 18). The fluorescence intensity at 335 nm decreased very quickly when pH increases from 1.78 to 7.04 (the thin lines in FIG. 18), and did not show further changes beyond pH 7 (the thick lines in FIG. 18). The fluorescence intensity at 513 nm increased very quickly when pH increased from 1.78 to 7.04 (thin lines in FIG. 18), and then decreased in the pH range of 7.04-10.54 (thick lines in FIG. 18). Almost no fluorescence was observed at 433 nm in the pH range between 1.78 and 7.04 (thin lines in FIG. 18). However, the fluorescence intensity at 433 nm increased very significantly when pH increased from 7.04 to 10.54 (thick lines in FIG. 18). It should be noted that while very significant changes were observed with the fluorescence, the absorption spectrum only showed minor pH-dependent variations.

The pH induced spectral changes at 335 nm in the absence of a sugar is similar to those in the presence of 50 mM fructose and glucose. An over 30-fold intensity decrease at 335 nm is observed when pH increases from 1.78 to 7.04. Plotting the intensity changes at 335 nm against pH reveals the first apparent $pK_a$ of 5.1 for 7 alone and in the presence of glucose, and 5.8 in the presence of 50 mM of fructose.

The pH profiles of the fluorescence intensity of 7 at 433 nm indicate that the second apparent $pK_a$ of 7 being about 9.0 in the absence of any sugar, 6.2 in the presence of fructose at 50 mM, 8.2 in the presence of 50 mM of glucose. It is reasonable to assign the first $pK_a$ to the aniline group and the second $pK_a$ to the boronic acid.

Figure 19:
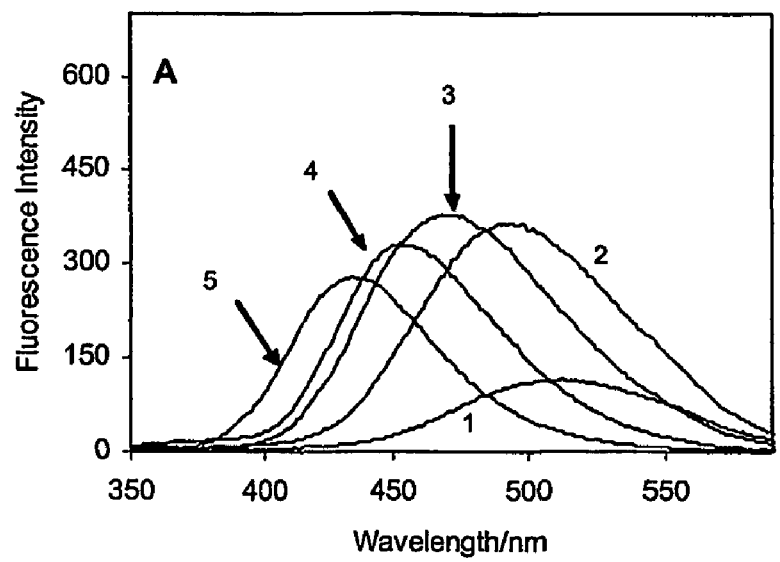
FIG. 19 shows the emission (A) and absorption (B) spectra of 5-DMANBA (7) ($1.0\times10^{-5}$ M) in different solvents (1: buffer; 2: MeOH-buffer (1:1, v/v); 3: MeOH; 4: EtOAc; 5: hexanes). Buffer: 0.1 M aqueous phosphate buffer at pH 7.4.
Figure 19:
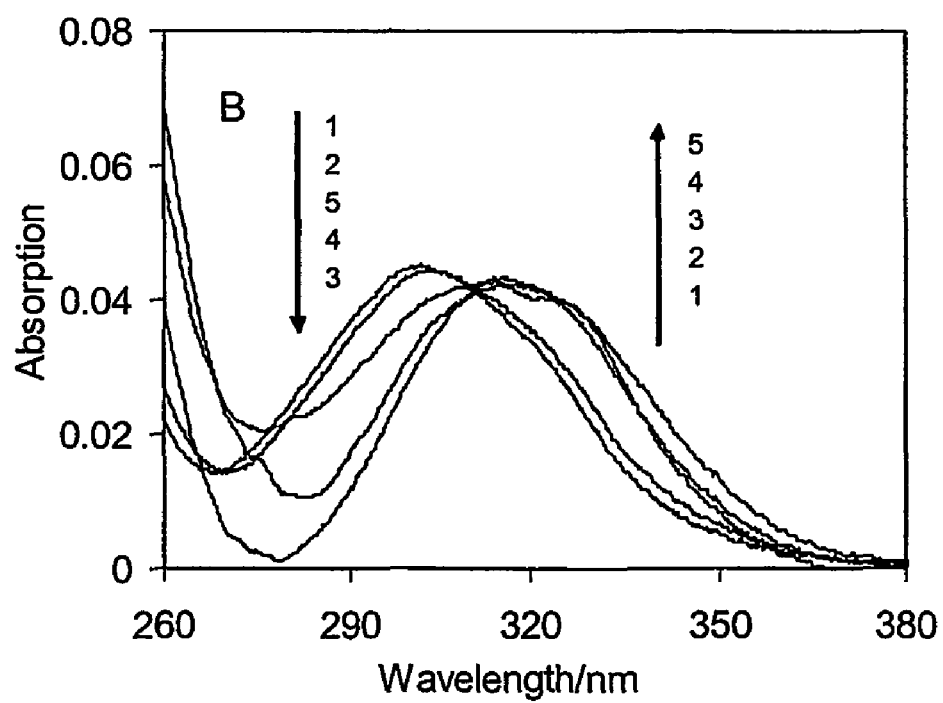

The study of the solvent effect on the emission and absorption spectra of 5-DMANBA (7) was carried out to gain a further understanding of the mechanism for the ratiometric fluorescence changes of compound 7. A large blue shift (80 nm) was observed in the emission spectra of compound 1 when the solvent polarity was decreased (513 nm in pH 7.4 0.1 M aqueous phosphate buffer and 433 nm in hexanes, FIG. 19A). However, the wavelength changes in the absorption spectra was much smaller in comparision (FIG. 19B). For example, the absorption maximum changed from 300 nm in aqueous phosphate buffer to 315 nm in hexanes. These solvent-induced fluorescent changes are characteristic of an excited-state charge-transfer (CT) in a polar solvent. The CT most likely occurs between the electron-donor dimethylamino group and the electron-acceptor boronic acid group. The $sp^2$-hybridized boron atom of the boronic acid group linked directly to the naphthalene can form a conjugated system with naphthalene and act as an electron acceptor group because of the empty p-orbital in the boron atom. Incorporation of a donor dimethylamino group on the same chromophore results in excited state charge transfer and the emission appears at a longer wavelength (513 nm for compound 1). Additionally, the sugar induced emission changes of compound 1 can also be explained through the CT mechanism. Addition of a sugar lowers the $pK_a$ of the boronic acid group and converts the neutral $sp^2$- to the anionic $sp^3$-hybridization. In the $sp^3$ state, boronic acid can no longer act as an electron-acceptor group. As a result, the CT process was turn off and the emission showed at a shorter wavelength (433 nm). The fact that the $\lambda_{em}$ for 7 is the same in hexanes as it is in PBS buffer in the presence of a sugar is also consistent with the disappearance of CT in hexanes, and in the presence of a sugar in PBS.

Example 6

Referring to scheme 2, the following synthetic procedure was used to produce compound 7 (compound 9 in Table 1).

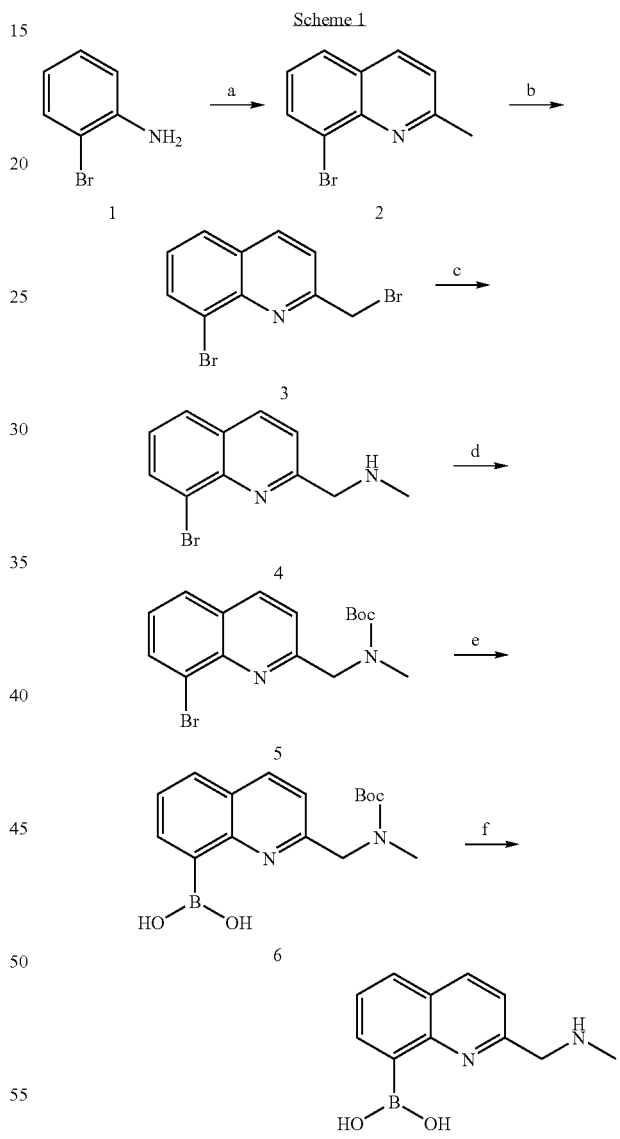

Reagents and conditions: a. Crotonaldehyde, 6 N HCl, reflux, 56%, b. NBS, AIBN, CCl$_4$, 39%, c. MeNH$_2$ (40%, wt), THF, 96%, d. (Boc)$_2$O, TEA, methanol, 97% e. Pd(dppf)$_2$CH$_2$Cl$_2$, bis(neopentyl glycolato)diboron, KOAc, DMSO, 90%, f. TFA, DCM, 98%.

8-Bromo-2-methyl-quinoline (2). To a refluxed solution of 2-bromoaniline (5.0 g, 29.1 mmol) in 6 N hydrochloric acid (15 mL) was added crotonaldehyde (2.2409 g, 32.0 mmol) drop wise. After heated under reflux for 8 h, the reaction mixture was cooled down and washed with 20 ml of ether, followed by addition of zinc chloride (3.95 g). The reaction mixture was stirred for 30 min at room temperature and another 15 min at 0° C. to give yellow solid. The solid was collected and washed with 3 N cold hydrochloric acid, and then suspended in 2-propanol (20 mL) and stirred for 5 min at room temperature. The solid was filtered and washed with 2-propanol until the washing becomes colorless, then washed with 20 mL of ether and dried with air. The solid was suspended in 15 mL of cold water and 5 mL of concentrated ammonium hydroxide was added. Shake it and then extract with 3×20 mL of ether. Dried over magnesium sulfate and concentrated to give a dark solid. Purification by chromatography (EtOAC/Hexanes 10:90) yielded a white solid product. (3.62 g, 56%) $^1$H NMR(400 MHz CDCl$_3$) δ8.02 (2H, t, J=8.4 Hz), 7.73 (1H, d, J=8 Hz), 7.33 (2H, t, J=8), 2.82 (3H, s); $^{13}$C NMR (300 MHz CDCl$_3$) δ160.2, 144.7, 136.4, 132.8, 127.6, 127.3, 125.9, 124.0, 122.7, 25.6; EIMS, m/z 221/223 (M/(M+2)); Anal. Calcd for C$_{10}$H$_8$BrN: C, 54.08; H, 3.63; N, 6.31. Found: C, 54.25; H, 3.41; N, 5.89.

8-Bromo-2-bromomethyl-quinoline (3). To a solution of 2 (2.5477 g, 11.47 mmol) in carbon tetrachloride (40 mL) was added NBS (2.2461 g, 12.62 mmol) and a little bit of AIBN followed by refluxing overnight under UV light. The mixture was filtered to remove the solid and concentrated to give a yellow solid. Purification by chromatography (hexanes/DCM 80:20) yielded a white solid.(1.33 g, 39%) $^1$H NMR (400 MHz CDCl$_3$) δ8.16 (1H, d, J=8.4 Hz), 8.05 (1H, d, J=7.2 Hz), 7.78 (1H, d, J=7.6 Hz), 7.65 (1H, d, J=8.4 Hz), 7.41 (1H, t, J=7.6 Hz), 4.78 (3H, s); $^{13}$C NMR (300 MHz CDCl$_3$) δ158.3, 144.7, 138.0, 133.9, 128.9, 127.7, 127.6, 125.1, 122.4, 34.6; EIMS, m/z 299/300/301 (M/M+1/M+2).

(8-Bromo-quinolin-2-ylmethyl)-methyl-amine (4). To a solution of 3 (1 g, 3.32 mmol) in THF (5 mL) was added methylamine (10.5 mL of 40% water solution). The solution was stirred for 30 min and then extracted with EtOAc (30 mL). The organic phase was washed with DI water (2×20 mL), dried and concentrated to give a red oil. Purification by chromatography (MeOH/DCM 1:99) yielded yellow solid. (0.8 g, 96%) $^1$H NMR (400 MHz CDCl$_3$) δ8.09 (1H, d, J=8.4 Hz), 8.02 (1H, d, J=7.2 Hz), 7.77 (1H, d, J=8 Hz), 7.49 (1H, d, J=8.4 Hz), 7.36 (1H, t, J=8.0 Hz), 4.12 (2H, s), 2.58 (3H, s).

(8-Bromo-quinolin-2-ylmethyl)-methyl-carbamic acid tert-butyl ester (5). To a solution of 4 (0.7501 g, 2.99 mmol) in methanol was added (Boc)$_2$O (1.4992 g, 6.87 mmol) and triethylamine (2.1 mL, 14.9 mmol). The mixture was stirred at rt for 2 h, and then concentrated in vacuum to remove all of the solvent. The residue was dissolved in DCM (20 mL) and then washed with DI water (2×10 mL) and brine (10 mL). The organic solution was dried over MgSO$_4$ and concentrated to give yellow oil. Purification by chromatography (hexanes/ EtOAc 10:90) yielded a light yellow oil. $^1$H NMR (400 MHz CDCl$_3$) δ8.16 (1H, t, J=8.4 Hz), 8.06 (1H, d, J=6.9 Hz), 7.80 (1H, d, J=7.8 Hz), 7.41 (2H, m), 4.81 (2H, s), 3.03 (3H, d, J=11.7 Hz), 1.4-1.6 (9H); $^{13}$C NMR (400 MHz CDCl$_3$) δ160.0, 144.9, 137.5, 133.4, 128.7, 127.7, 126.9, 124.9, 120.7, 119.8, 80.1, 55.5, 35.2, 28.7; ESIMS, m/z 351/353 (M/(M+2),100); Anal Calcd for C16H19BrN2O2: C, 54.71; H, 5.45; N, 7.98. Found: C, 54.97; H, 5.62; N, 7.75.

(6). To a flask charged with 5 (0.4440 g, 1.26 mmol), bis(neopentyl glycolato)diboron (0.3427 g, 1.52 mmol), Pd(dppf)$_2$CH$_2$Cl$_2$ (0.0310 g, 0.038 mmol) and KOAc (0.3722 g, 3.79 mmol) in a nitrogen atmosphere was added anhydrous DMSO (10 mL). The mixture was stirred at 80° C. overnight, then poured into DCM (20 mL) and washed with DI water (4×30 mL). The organic solution was dried over MgSO$_4$ and concentrated to give a dark oil. Purification by chromatography (MeOH/DCM, 1:99) yielded a yellow oil (0.3313 g, 82%). $^1$H NMR (400 MHz CDCl$_3$) δ8.45 (1H, d, J=5.4 Hz), 8.14 (1H, d, J=6.6 Hz), 7.97 (1H, d, J=8.1 Hz), 7.623 (1H, t, J=7.5 Hz), 7.49 (1H, d, J=8.4 Hz), 4.80 (2H, d, J=6.0 Hz), 3.09 (3H, d, J=4.2 Hz), 1.3-1.5 (9H); $^{13}$C NMR (400 MHz CDCl$_3$) δ157.3, 156.8, 156.2, 150.3, 139.4, 137.4, 129.7, 127.2, 126.6, 119.1, 118.9, 80.5, 74.7, 34.7, 27.4, 23.9; ESIMS, m/z 317, M+1.

(7). To a solution of 6 (0.2501 g, 0.79 mmol) in DCM (20 mL) was added TFA (5 mL). The solution was stirred for 1 h, and then concentrated in vacuum to give a yellow oil. This compound is not stable in neutral, so no further purification preformed. $^1$H NMR (300 MHz CDCl$_3$) δ8.35 (1H, d, J=8.4 Hz), 8.12 (1H, d, J=6.0 Hz), 7.87 (1H, d, J=6.0 Hz), 7.60 (1H, t, J=9.0 Hz), 7.44 (1H, d, J=8.4 Hz), 4.47 (2H, s), 2.94 (3H, s).

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. The compound selected from the group consisting of 2-((methylamino)methyl)quinoline-8-ylboronic acid.

2. A pharmaceutical composition comprising the compound of claim 1 and a pharmaceutically acceptable carrier.

* * * * *